US012410222B2

(12) United States Patent
Tavernier et al.

(10) Patent No.: US 12,410,222 B2
(45) Date of Patent: Sep. 9, 2025

(54) FUSOKINES INVOLVING CYTOKINES WITH STRONGLY REDUCED RECEPTOR BINDING AFFINITIES

(71) Applicants: VIB VZW, Ghent (BE); Universiteit Gent, Ghent (BE); Centre National De Le Recherche Scientifique, Paris (FR); Université De Montpellier, Montpellier (FR); Centre Hospitalier Regional Universitaire de Montpellier, Montpellier (FR)

(72) Inventors: Jan Tavernier, Balegem (BE); Jennyfer Bultinck, Ledeberg (BE); Sarah Gerlo, Ghent (BE); Gilles Uze, Montpellier (FR); Franciane Paul, Montpellier (FR); Yann Bordat, Montpellier (FR)

(73) Assignees: VIB VZW, Ghent (BE); Universiteit Gent, Ghent (BE); Centre National De Le Recherche Scientifque, Paris (FR); Universitè De Montpellier, Montpellier (FR); Centre Hospitalier Regional Universitaire de Montpellier, Montpellier (FR)

( * ) Notice: Subject to any disclaimer, the term of this patent is extended or adjusted under 35 U.S.C. 154(b) by 323 days.

(21) Appl. No.: 17/733,026

(22) Filed: Apr. 29, 2022

(65) Prior Publication Data

US 2023/0054612 A1 Feb. 23, 2023

Related U.S. Application Data

(60) Continuation of application No. 16/103,302, filed on Aug. 14, 2018, now Pat. No. 11,358,997, which is a division of application No. 14/905,343, filed as application No. PCT/EP2014/064227 on Jul. 3, 2014, now Pat. No. 10,640,542.

(30) Foreign Application Priority Data

Jul. 18, 2013 (EP) .................................... 13306034

(51) Int. Cl.

| | |
|---|---|
| ***C07K 14/52*** | (2006.01) |
| ***A61K 38/19*** | (2006.01) |
| ***A61K 38/20*** | (2006.01) |
| ***A61K 38/22*** | (2006.01) |
| ***A61P 37/04*** | (2006.01) |
| ***C07K 14/525*** | (2006.01) |
| ***C07K 14/545*** | (2006.01) |
| ***C07K 14/56*** | (2006.01) |
| ***C07K 14/575*** | (2006.01) |

(52) U.S. Cl.

CPC .......... *C07K 14/521* (2013.01); *A61K 38/195* (2013.01); *A61K 38/2006* (2013.01); *A61P 37/04* (2018.01); *C07K 14/52* (2013.01); *C07K 14/523* (2013.01); *C07K 14/525* (2013.01); *C07K 14/545* (2013.01); *C07K 14/56* (2013.01); *C07K 14/5759* (2013.01); *A61K 38/19* (2013.01); *A61K 38/2264* (2013.01); *C07K 2319/00* (2013.01); *C07K 2319/33* (2013.01); *C07K 2319/74* (2013.01)

(58) Field of Classification Search

None

See application file for complete search history.

(56) References Cited

U.S. PATENT DOCUMENTS

| | | | |
|---|---|---|---|
| 5,914,254 | A | 6/1999 | Mascarenhas et al. |
| 8,980,267 | B2 | 3/2015 | Grewal et al. |
| 9,139,634 | B2 | 9/2015 | Morrison et al. |
| 2010/0172868 | A1 | 7/2010 | Morrison et al. |
| 2010/0297076 | A1 | 11/2010 | Morrison et al. |
| 2011/0104112 | A1 | 5/2011 | Morrison et al. |
| 2011/0274658 | A1 | 11/2011 | Silver et al. |
| 2013/0183298 | A1 | 7/2013 | Le et al. |
| 2015/0139951 | A1 | 5/2015 | Grewal et al. |

FOREIGN PATENT DOCUMENTS

| | | | |
|---|---|---|---|
| WO | 9102754 | A1 | 3/1991 |
| WO | 2006053883 | A1 | 5/2006 |
| WO | 2006115800 | A2 | 11/2006 |
| WO | 2008014612 | A1 | 2/2008 |
| WO | 2008124086 | A2 | 10/2008 |
| WO | 2009003145 | A1 | 12/2008 |
| WO | 2009039409 | A1 | 3/2009 |
| WO | 2010036918 | A2 | 4/2010 |
| WO | 2010066740 | A1 | 6/2010 |
| WO | 2011020783 | A2 | 2/2011 |
| WO | 2011029870 | A1 | 3/2011 |
| WO | 2012170072 | A1 | 12/2012 |
| WO | 2013059885 | A2 | 5/2013 |
| WO | 2013107791 | A1 | 7/2013 |
| WO | 2013134138 | A1 | 9/2013 |

OTHER PUBLICATIONS

Acres, B., et al., "Fusokine Interleukin-2/Interleukin-18, a Novel Potent Innate and Adaptive Immune Stimulator with Decreased Toxicity", Cancer Res., vol. 65, No. 20, (2005), pp. 9536-9546.

(Continued)

*Primary Examiner* — Ruixiang Li

(74) *Attorney, Agent, or Firm* — Morgan, Lewis & Bockius LLP

(57) ABSTRACT

The present invention relates to a fusion protein comprising at least two cytokines, of which at least one is a modified cytokine with a strongly reduced binding affinity to its receptor, or to one of its receptors. Preferably, both cytokines are connected by a linker, preferably a GGS linker. The invention relates further to said fusion protein for use in treatment of diseases.

2 Claims, 13 Drawing Sheets

Specification includes a Sequence Listing.

(56) References Cited

OTHER PUBLICATIONS

Baba, M., et al., "Identification of CCR6, the Specific Receptor for a Novel Lymphocyte-Directed CC Chemokine ARC", The Journal of Biological Chemistry vol. 272, No. 23, (1997), pp. 14893-14898.
Camacho, N.P., et al., "Structure of an Interleukin-1βMutant With Reduced Bioactivity Shows Multiple Subtle Changes in Conformation That Affect Protein-Protein Recognition", Biochemistry, vol. 32, No. 34, (1993), pp. 8749-8757.
Coulstock, E., et al., "Liver-Targeting of Interferon-Alpha with Tissue Specific Domain Antibodies." Plos One, vol. 8, No. 2, (2013), pp. 1-11.
De Bruyn, M., et al., "Antibody-Based Fusion Proteins to Target Death Receptors in Cancer", Cancer Letters, vol. 332, (2013), pp. 175-183.
Dijkmans, R., et al., "Murine Interferon-γ/Interleukin-1 Fusion Proteins Used as Antigens for the Generation of Hybridomas Producing Monoclonal Anti-Interleukin-1 Antibodies", Cytokine, vol. 3, No. 2, (1991), pp. 134-140.
Dimitrov, D. S., "Engineered CH2 Domains (Nanoantibodies)", mAbs, Landes Bioscience, vol. 1, No. 1, (2009), pp. 26-28.
Frey, K., et al., "Antibody-Based Targeting of Interferon-Alpha to the Tumor Neovasculature: A Critical Evaluation", Integrative Biology, vol. 3, (2011), p. 468-478.
Garcin, G., et al., "High Efficiency Cell-Specific Targeting of Cytokine Activity", Nature Communications, (2014), pp. 1-9.
Holler, N., et al: "Two Adjacent Trimeric Fas Ligands are Required for Fas Signaling and Formation of a Death- Inducing Signaling Complex", Molecular and Cellular Biology, vol. 23, No. 4, (2003), pp. 1428-1440.
Huang, T., et al., "A Trimeric Anti-HER2/neu ScFv and Tumor Necrosis Factor-[alpha] Fusion Protein Induces HER2/Neu Signaling and Facilitates Repair of Injured Epithelia", The Journal of Pharmacology and Experimental Therapeutics, vol. 316, No. 3, (2006), pp. 983-991.
International Search Report and Written Opinion in PCT/EP2013/050787, dated Jun. 14, 2013.
International Search Report and Written Opinion PCT/EP2014/063976, dated Oct. 29, 2014.
International Search Report and Written Opinion PCT/EP2014/064227, dated Feb. 5, 2015.
International Search Report and Written Opinion PCT/EP2014/064283, dated Oct. 1, 2014.
International Search Report and Written Opinion PCT/EP2014/065554, dated Oct. 30, 2014.
Krippner-Heidenreich, A., et al: "Single-Chain TNF, a TNF Derivative with Enhanced Stability and Antitumoral Activity", The Journal of Immunology, vol. 180, (2008), pp. 8176-8183.
Masci, P. et al., "New and Modified Interferon alfas: Preclinical and Clinical Data", Current Oncology Reports, vol. 5, (2003), pp. 108-113.
Pan, M., et al., "Mutation of the IFNAR-1 Receptor Binding Site of Human IFN-[alpha]2 Generates Type I IFN Competitive Antagonists", Biochemistry, vol. 47, (2008), pp. 12018-12027.
Penafuerte, C., et al., "The Human Ortholog of Granulocyte Macrophage Colony-Stimulating Factor and Interleukin-2 Fusion Protein Induces Potent Ex Vivo Natural Killer Cell Activation and Maturation", Cancer Res, vol. 69, No. 23, (2009), pp. 9020-9028.
Rafei, M., et al., "A MCP1 Fusokine with CCR2-Specific Tumoricidal Activity", Molecular Cancer, vol. 10, No. 121, (2011), pp. 1-11.
Rafei, M., et al., "An Engineered GM-CSF-CCL2 Fusokine is a Potent Inhibitor of CCR2-Driven Inflammation as Demonstrated in a Murine Model of Inflammatory Arthritis", The Journal of Immunology, vol. 183, (2009), pp. 1759-1766.
Roisman, LC., et al., "Structure of the Interferon-Receptor Complex Determined by Distant Constraints from Double Mutant Cycles and Flexible Docking", PNAS, vol. 98, No. 23, (2001), pp. 13231-13236.
Rovero S et al., "Insertion of the DNA for the 163-171 Peptide of IL 1β Enables a DNA Vaccine Encoding p185neu to Inhibit Mammary Carcinogenesis in Her-2/neu Transgenic BALB/c Mice", Gene Therapy, vol. 8, (2001), pp. 447-452.
Schutyser, E., et al., "The CC Chemokine CCL20 and its Receptor CCR6", Cytokine & Growth Factor Reviews, vol. 14, (2003), pp. 409-426.
Weber, H., et al., "Single Amino Acid Changes that Render Human IFN-[alpha]2 Biologically Active on Mouse Cells", The EMBO Journal, vol. 6, No. 3, (1987), pp. 591-598.
Acosta-Rodriguez EV, Napolitani G, Lanzavecchia A and Sallusto F. (2007) "Interleukins 1beta and 6 but not transforming growth factor-beta are essential for the differentiation of interleukin 17-producing human T helper cells". Nat Immunol. 8, 942-9.
Bachem A, Hartung E, Guttler S, Mora A, Zhou X, Hegemann A, Plantinga M, Mazzini E, Stoitzner P, Gurka S, Henn V, Mages HW and Kroczek RA. (2012). "Expression of XCR1 Characterizes the Batf3-Dependent Lineage of Dendritic Cells Capable of Antigen Cross-Presentation". Front Immunol. 3, 214. doi: 10.3389.
Ben-Sasson SZ, Caucheteux S, Crank M, Hu-Li J and Paul WE. (2011). "IL-1 acts on T cells to enhance the magnitude of in vivo immune responses". Cytokine, 56, 122-5.
Bono MR, Benech P, Coullin P, Alcaide-Loridan C, Grisard MC, Join H, Fischer DG and Fellous M. (1989). Characterization of human IFN-gamma response using somatic cell hybrids of hematopietic and nonhematopoietic origin. Somat. Cell Mol. Genet. 15, 513-23.
Brecht A., Gauglitz G., Polster J. (1993). Interferometric immunoassay in a FIA-system—A sensitive and rapid approach in label-free immunosensing. , Biosens Bioelectron 8 : 387-392.
Crozat K, Guiton R, Contreras V, Feuillet V, Dutertre CA, Ventre E, Vu Manh TP, Baranek T, Storset AK, Marvel J, Boudinot P, Hosmalin A, Schwartz-Cornil I and Dalod M. (2010). The XC chemokine receptor 1 is a conserved selective marker of mammalian cells homologous to mouse CD8alpha+ dendritic cells. J. Exp. Med. 207, 1283-1292.
Donahue RE, Seehra J, Metzger M, Lefebvre D, Rock B, Carbone S, Nathan DG, Garnick M, Sehgal PK, Laston D, et al. (1988). Human IL-3 and GM-CSF act synergistically in stimulating hematopoiesis in primates. Science 241, 1820-1823.
Dorner BG, Dorner MB, Zhou X, Opitz C, Mora A, Guttler S, Hutloff A, Mages HW, Ranke K, Schaefer M, Jack RS, Henn V and Kroczek RA. (2009). Selective expression of the chemokine receptor XCR1 on cross-presenting dendritic cells determines cooperation with CD8+ T cells. Immunity 31, 823-833.
Dunne A, Ross PJ, Pospisilova E, Masin J, Meaney A, Sutton CE, Iwakura Y, Tschopp J, Sebo P and Mills KH. (2010) Inflammasome activation by adenylate cyclase toxin directs Th17 responses and protection against Bordetella pertussis. J Immunol. 185, 1711-9.
Fuertes MB, Kacha AK, Kline J, Woo SR, Kranz DM, Murphy KM and Gajewski TF (2011). Host type I IFN signals are required for antitumor CD8+ T cell responses through CD8{alpha}+ dendritic cellsJ. Exp. Med. 208, 2005-2016.
Gaffen SL. (2011). Recent advances in the IL-17 cytokine family. Curr Opin Immunol. 23, 613-9.
Gajewski TF, Fuertes MB and Woo SR (2012). Innate immune sensing of cancer: clues from an identified role for type I IFNs. Cancer Immunol Immunother. 61, 1343-7.
Gillies SD, Lan Y, Brunkhorst B, Wong WK, Li Y, Lo KM. (2002). Bi-functional cytokine fusion proteins for gene therapy and antibody-targeted treatment of cancer. Cancer Immunol Immunother 51, 449-460.
Halaas JL, Gajiwala KS, Maffei M, Cohen SL, Chait BT, Rabinowitz D, Lallone RL, Burley SK and Friedman JM. (1995). Weight-reducing effects of the plasma protein encoded by the obese gene. Science, 269, 543-6.
Hehlgans, T and Pfeffer, K (2005). The intriguing biology of the tumour necrosis factor/tumour necrosis factor receptor superfamily: players, rules and the games. Immunology. 115, 1-20.
Hieshima K, Imai T, Opdenakker G, Van Damme J, Kusuda J, Tei H, Sakaki Y, Takatsuki K, Miura R, Yoshie O and Nomiyama H. (1997). Molecular cloning of a novel human CC chemokine liver and activation-regulated chemokine (LARC) expressed in liver. Chemotactic activity for lymphocytes and gene localization on chromosome 2. J Biol Chem. 272, 5846-53.

(56) References Cited

OTHER PUBLICATIONS

Higgins SC, Jarnicki AG, Lavelle EC and Mills KH. (2006). TLR4 mediates vaccine-induced protective cellular immunity to Bordetella pertussis: role of IL-17-producing T cells. J Immunol. 177, 7980-9.

Idriss HT & Naismith JH (2000). TNF alpha and the TNF receptor superfamily: structure-function relationship(s). Microscopy research and technique 50, 184-95.

Tikuni N, Lam QL, Lu L, Matarese G, La Cava A. (2008). Leptin and Inflammation. Curr Immunol.

Jahn T, Zuther M, Friedrichs B, Heuser C, Guhlke S, Abken H, Hombach AA (2012). An IL12-IL2-antibody fusion protein targeting Hodgkin's lymphoma cells potentiates activation of NK and T cells for an anti-tumor attack. PLoS One 7:e44482.

Khader SA, Bell GK, Pearl JE, Fountain JJ, Rangel-Moreno J, Cilley GE, Shen F, Eaton SM, Gaffen SL, Swain SL, Locksley RM, Haynes L, Randall TD and Cooper AM. (2007). IL-23 and IL-17 in the establishment of protective pulmonary CD4+ T cell responses after vaccination and during Mycobacterium tuberculosis challenge. Nat Immunol. 8, 369-77.

Lu J, Peng Y, Zheng ZJ, Pan JH, Zhang Y, Bai Y (2008). EGF-IL-18 fusion protein as a potential anti-tumor reagent by Induction of immune response and apoptosis in cancer cells. Cancer Lett 260, 187-197.

Murzin AG, Lesk AM & Chothia C (1992). B-Trefoil fold: Patterns of structure and sequence in the Kunitz inhibitors Interleukins-1β and 1α and fibroblast growth factors. Journal of Molecular Biology 223, 531-543.

Nicola NA & Hilton DJ (1998). General classes and functions of four-helix bundle cytokines. Advances in protein chemistry 52, 1-65.

Nomiyama H, Osada N and Yoshie O. (2013). Systematic classification of vertebrate chemokines based on conserved synteny and evolutionary history. Genes Cells. 18,1-16.

O'Shaughnessy JA, Tolcher A, Riseberg D, Venzon D, Zujewski J, Noone M, Gossard M, Danforth D, Jacobson J, Chang V, Goldspiel B, Keegan P, Giusti R and Cowan KH. (1996). Prospective, randomized trial of 5-fluorouracil, leucovorin, doxorubicin, and cyclophosphamide chemotherapy in combination with the interleukin-3/granulocyte-macrophage colony-stimulating factor (GM-CSF) fusion protein (PIXY321) versus GM-CSF in patients with advanced breast cancer. Blood 87, 2205-2211.

Rafei M, Wu JH, Annabi B, Lejeune L, François M and Galipeau J (2007). A GMCSF and IL-15 fusokine leads to paradoxical immunosuppression in vivo via asymmetrical JAK/STAT signaling through the IL-15 receptor complex. Blood 109, 2234-2242.

Rafei M, Hsieh J, Zehntner S, Li M, Forner K, Birman E, Boivin MN, Young YK, Perreault C and Galipeau J. (2009a). A granulocyte-macrophage colony-stimulating factor and interleukin-15 fusokine induces a regulatory B cell population with immune suppressive properties. Nat Med 15, 1038-1045.

Rafei M, Campeau PM, Wu JH, Birman E, Forner K, Boivin MN and Galipeau J. (2009b) Selective inhibition of CCR2 expressing lymphomyeloid cells in experimental autoimmune encephalomyelitis by a GM-CSF-MCP1 fusokine. J Immunol. 182, 2620-7.

Shaw MH, Kamada N, Kim YG and Nuñez G. (2012) Microbiota-induced IL-1β, but not IL-6, is critical for the development of steady-state TH17 cells in the intestine. J Exp Med. 209, 251-8.

Singh SP, Zhang HH, Foley JF, Hedrick MN and Farber JM. (2008) Human T cells that are able to produce IL-17 express the chemokine receptor CCR6. J Immunol. 180, 214-21.

Scatchard G. (1949). Ann New York Acad Sci 51, 660-72.

Stagg J, Wu JH, Bouganim N and Galipeau J. (2004). Granulocyte-macrophage colony-stimulating factor and Interleukin-2 fusion cDNA for cancer gene immunotherapy. Cancer Res 64, 8795-8799.

Sun PD & Davies DR. (1995). The cystine-knot growth-factor superfamily. Annual review of biophysics and biomolecular structure 24, 269-91.

Sutton C, Brereton C, Keogh B, Mills KH and Lavelle EC. (2006). A crucial role for interleukin (IL)-1 in the induction of IL-17-producing T cells that mediate autoimmune encephalomyelitis. J Exp Med. 203, 1685-91.

Williams P, Bouchentouf M, Rafei M, Romieu-Mourez R, Hsieh J, Boivin MN, Yuan S, Forner KA, Birman E and Galipeau J. (2010a). A dendritic cell population generated by a fusion of GM-CSF and IL-21 induces tumor-antigen-specific immunity. J Immunol. 185, 7358-66.

Williams P, Rafei M, Bouchentouf M, Raven J, Yuan S, Cuerquis J, Forner KA, Birman E and Galipeau J. (2010b). A fusion of GMCSF and IL-21 initiates hypersignaling through the IL-21Ralpha chain with immune activating and tumoricidal effects in vivo. Mol Ther 18, 1293-1301.

Ye P, Rodriguez FH, Kanaly S, Stocking KL, Schurr J, Schwarzenberger P, Oliver P, Huang W, Zhang P, Zhang J, Shellito JE, Bagby GJ, Nelson S, Charrier K, Peschon JJ and Kolls JK. (2001). Requirement of interleukin 17 receptor signaling for lung CXC chemokine and granulocyte colony-stimulating factor expression, neutrophil recruitment, and host defense. J Exp Med. 194, 519-27.

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: Linker

<400> SEQUENCE: 1

Gly Gly Gly Gly Ser
1               5


<210> SEQ ID NO 2
<211> LENGTH: 32
<212> TYPE: DNA
<213> ORGANISM: Artificial Sequence
<220> FEATURE:
<223> OTHER INFORMATION: Primer

<400> SEQUENCE: 2

ggggggaat tcatgagact tctcctcctg ac                                    32


<210> SEQ ID NO 3
<211> LENGTH: 34
<212> TYPE: DNA
<213> ORGANISM: Artificial Sequence
<220> FEATURE:
<223> OTHER INFORMATION: Primer

<400> SEQUENCE: 3

ggggggtccg gaggcccagt cagggttatc gctg                                 34


<210> SEQ ID NO 4
<211> LENGTH: 39
<212> TYPE: DNA
<213> ORGANISM: Artificial Sequence
<220> FEATURE:
<223> OTHER INFORMATION: Primer

<400> SEQUENCE: 4

gcggcagcgc ccctgtcgga agcttgaact gcaccctgc                            39


<210> SEQ ID NO 5
<211> LENGTH: 37
<212> TYPE: DNA
<213> ORGANISM: Artificial Sequence
<220> FEATURE:
<223> OTHER INFORMATION: Primer
```

-continued

<400> SEQUENCE: 5
ctgcgggaca gccaggggaa gagcctggtc atgagcg 37

<210> SEQ ID NO 6
<211> LENGTH: 38
<212> TYPE: DNA
<213> ORGANISM: Artificial Sequence
<220> FEATURE:
<223> OTHER INFORMATION: Primer

<400> SEQUENCE: 6
cgagctgaag gcactggctc ttcagggcca ggacatgg 38

<210> SEQ ID NO 7
<211> LENGTH: 38
<212> TYPE: DNA
<213> ORGANISM: Artificial Sequence
<220> FEATURE:
<223> OTHER INFORMATION: Primer

<400> SEQUENCE: 7
gaaggcactg catctgggtg gccaggacat ggaacagc 38

<210> SEQ ID NO 8
<211> LENGTH: 49
<212> TYPE: DNA
<213> ORGANISM: Artificial Sequence
<220> FEATURE:
<223> OTHER INFORMATION: Primer

<400> SEQUENCE: 8
ccccaagaac taccccaagg caaagatgga aaagcgcttc gtgttcaac 49

<210> SEQ ID NO 9
<211> LENGTH: 39
<212> TYPE: DNA
<213> ORGANISM: Artificial Sequence
<220> FEATURE:
<223> OTHER INFORMATION: Primer

<400> SEQUENCE: 9
gcagggtgca gttcaagctt ccgacagggg cgctgccgc 39

<210> SEQ ID NO 10
<211> LENGTH: 37
<212> TYPE: DNA
<213> ORGANISM: Artificial Sequence
<220> FEATURE:
<223> OTHER INFORMATION: Primer

<400> SEQUENCE: 10
cgctcatgac caggctcttc ccctggctgt cccgcag 37

<210> SEQ ID NO 11
<211> LENGTH: 38
<212> TYPE: DNA
<213> ORGANISM: Artificial Sequence
<220> FEATURE:
<223> OTHER INFORMATION: Primer

<400> SEQUENCE: 11
ccatgtcctg gccctgaaga gccagtgcct tcagctcg 38

<210> SEQ ID NO 12

-continued

```
<211> LENGTH: 38
<212> TYPE: DNA
<213> ORGANISM: Artificial Sequence
<220> FEATURE:
<223> OTHER INFORMATION: Primer

<400> SEQUENCE: 12

gctgttccat gtcctggcca cccagatgca gtgccttc                    38


<210> SEQ ID NO 13
<211> LENGTH: 49
<212> TYPE: DNA
<213> ORGANISM: Artificial Sequence
<220> FEATURE:
<223> OTHER INFORMATION: Primer

<400> SEQUENCE: 13

gttgaacacg aagcgctttt ccatctttgc cttggggtag ttcttgggg         49


<210> SEQ ID NO 14
<211> LENGTH: 38
<212> TYPE: DNA
<213> ORGANISM: Artificial Sequence
<220> FEATURE:
<223> OTHER INFORMATION: Primer

<400> SEQUENCE: 14

gcagatctgt cgacatccag aaagtccagg atgacacc                    38


<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15

cgatgcggcc gcacattcag ggctaacatc caactgt                     37
```

FUSOKINES INVOLVING CYTOKINES WITH STRONGLY REDUCED RECEPTOR BINDING AFFINITIES

The present invention relates to a fusion protein comprising at least two cytokines, of which at least one is a modified cytokine with a strongly reduced binding affinity to its receptor, or to one of its receptors. Preferably, both cytokines are connected by a linker, preferably a GGS linker. The invention relates further to said fusion protein for use in treatment of diseases.

Cytokines are small secreted or membrane-bound proteins which play a crucial role in intercellular communication. Cytokine binding to its cognate receptor complex triggers a cascade of intracellular signaling events that enables the cell to sense and respond to its surroundings according to the needs of the cell, tissue and organ of which it is part of. They are characteristically pleiotropic, meaning that they provoke a broad range of responses depending on the nature and the developmental state of the target cell. Moreover, some of them are highly redundant as several cytokines have overlapping activities, which enable them to functionally compensate for mutual loss. Cytokine activities can be autocrine, paracrine or endocrine causing a faint boundary between the designated term cytokine, peptide hormone and growth factor.

Six different structural classes of cytokines are known: the α-helical bundle cytokines which comprises most interleukins, colony stimulating factors and hormones like growth hormone and leptin (Nicola and Hilton, 1998), the trimeric tumor necrosis factor (TNF) family (Idriss and Naismith, 2000), the cysteine knot growth factors (Sun and Davies, 1995), the β-trefoil fold group that includes the interleukin-1 family (Murzin et al., 1992), the interleukin 17 (IL-17) family (Gaffen, 2011), and the chemokines (Nomiyama et al., 2013).

Several cytokines have found important clinical applications. Examples include erythropoietin (Epo), granulocyte colony-stimulating factor (G-CSF), interferons α2 and -β, and growth hormone. Conversely, often as a consequence of their pro-inflammatory nature, antagonizing selected cytokines also finds specific medical applications. Prime examples here are the strategies to block TNFα activity to combat autoimmune diseases such as rheumatoid arthritis. Because of these successes, strategies to optimize cytokine activities in the clinic are being explored. These include optimized half-life, reduced immunogenicity, targeted delivery to specific cell types and genetic fusions of two cytokines, so-called fusokines.

Fusokines are artificial combinations of two different cytokines which are genetically linked using a linker sequence. The first example of a fusokine is pIXY321 or pixykine which is a fusion protein of granulocyte-macrophage colony-stimulating factor (GMCSF) and IL-3 (Donahue et al., 1988) that showed superior hematopoietic and immune effects compared to either cytokine alone. This effect could be explained by enhanced binding to their respective receptor complexes. Of note, both receptors share the signaling βc subunit, precluding synergistic effects at the signal transduction level. In a Phase III clinical trial, pIXY321 did not show superior properties when compared to GM-CSF alone (O'Shaughnessy et al., 1996). GM-CSF-based fusokines with cytokines of the IL-2 family were explored as well. These cytokines all signal through receptor complexes comprising the γc subunit. Examples of such fusokines with GM-CSF include IL-2 (Stagg et al., 2004), IL-15 (Rafei et al., 2007) and IL-21 (Williams et al., 2010a), aka as GIFT2, -15 and -21. Synergistic effects could be expected both at the signaling level (i.e. synergistic effects within a target cell) and cellular level (i.e. synergistic effects between different target cell types). For example, GIFT2 induced more potent activation of NK cells compared to the combination of the unfused cytokines (Penafuerte et al., 2009) and GIFT15 induced an unanticipated, potent immune-suppressive B-cell population (Rafei et al., 2009a). Likewise, GIFT21 exerted unexpected proinflammatory effects on monocytic cells (Williams et al, 2010b). Another example of a fusokine that combines α-helical cytokines is IL-2/IL-12 (Gillies et al., 2002; Jahn et al, 2012).

Another class of fusokines combines cytokines from different structural families. Examples include the fusion of IL-18 (a member of the IL-1 cytokine family) and IL-2 (Acres et al., 2005) and the fusion between IL-18 and EGF (epidermal growth factor). Since overexpression of the EGFR is often observed on certain tumor cell types, the latter fusokine offers the possibility to target the IL-18 activity to EGFR+ tumor cells (Lu et al., 2008). Fusions between α-helical bundle cytokines and chemokines were also explored in greater detail. Chemokines often act using concentration gradients to steer migration of immune cells to sites of infection and inflammation. Many chemokine receptors display a restricted expression pattern allowing targeting to selected (immune) cells. Moreover, signaling via the serpentine, G-protein coupled chemokine receptors is fundamentally different from pathways activated by the α-helical bundle cytokine receptor complexes and synergetic positive and negative cross-talk mechanisms could be expected. Of note, designed N-terminally truncated versions of chemokines can retain their receptor binding properties but display antagonistic behavior. An example is a fusokine between GM-CSF and a N-terminally truncated CCL2 lacking the first 5 N-terminal amino-acids, aka GMME1 (Rafei et al., 2009b). This fusokine induced the apoptosis of inflammatory CCR2+ cells and mice treated with GMME1 displayed reduced experimentally-induced autoimmune disease scores including EAE and CIA for multiple sclerosis (Rafei et al., 2009b) and rheumatoid arthritis (Rafei et al., 2009c), respectively. Likewise, this fusokine induced apoptosis of CCR2+ tumor cells (Rafei et al., 2011).

However, fusions between a wild-type cytokine and a mutant cytokine with strongly reduced affinity for its cognate receptor complex were not explored before. The advantage of this approach is that the possible systemic toxicity of the wild type cytokine is eliminated. Surprisingly, we found that such fusokines allow cell-specific targeting of cytokine activities whereby such mutant cytokine can regain its activity on the targeted cells, without the negative effect of wild type cytokines. The general applicability of the principle has been demonstrated using three fusokines each composed of two cytokines from structurally different cytokine classes, as exemplified below.

XCL1/IFNα2-Mutant

XCL1 is a 93 amino acids chemokine secreted by $CD8^+$ T cells, Th1 cell-polarized $CD4^+$ T cells and NK cells. It interacts with XCR1, a chemokine receptor exclusively expressed by dendritic cells. In mice, XCR1 is expressed in the large majority of splenic $CD11c^+$ $CD8\alpha^+$ dendritic cells whereas only a very minor subset of $CD8\alpha^-$ dendritic cells expresses this receptor (Dorner et al. 2009). XCR1 is a conserved selective marker of mammalian cells (including human cells) homologous to mouse $CD8\alpha^+$ dendritic cells (Crozat et al. 2010). Interestingly it has been shown that the action of type I interferon (IFNα/β) on this dendritic cell subset is critical for the innate immune recognition of a growing tumor in mice (Fuertes et al. 2011).

Systemic IFNα therapy has considerable toxicity, including side effects such as severe fatigue, fever, chills, depression, thyroid dysfunction, retinal disease, hair loss, dry skin, rash, itching and bone marrow suppression. It would thus be highly worthwhile to target IFN activity toward only the cellular population which should be treated with IFN. For application in antitumor therapies, targeting the population of XCR1-expressing dendritic cells is highly desirable since these cells are specialized in antigen cross-presentation (Bachem et al. 2012). Many experimental data suggest that the XCR1-expressing dendritic cell population represents the key cellular population which must react with type I IFN in the tumor microenvironment in order to initiate the immune responses which ultimately will allow tumor destruction and immunization (Gajewski et al. 2012).

The human IFNα2-Q124R mutant has a high affinity for the murine IFNAR1 chain and a low affinity for the murine IFNAR2 chain (Weber et al., 1987). It displays a very low activity on murine cells and hence represents a prototype of an engineered type I IFN subtype suitable to target IFN activity on selected mouse cells (PCT/EP2013/050787).

CCL20/IL1β

The CC chemokine CCL20, also known as liver and activation-regulated chemokine (LARC), macrophage inflammatory protein-3α (MIP-3α) or Exodus-1 is a 96 AA protein that is predominantly expressed in liver and lymphoid tissue (Hieshima et al., 1997). Upon secretion, CCL20 exerts its activity by binding to the CC chemokine receptor 6 (CCR6), which belongs to the G-protein coupled receptor (GPCR) 1 family (Baba et al., 1997). CCR6 expression is reported on different leukocyte subsets but is best documented for the Th17 cell population (Singh et al., 2008). Normal Th17 function is indispensable for protective immunity against a range of pathogens, including *Mycobacterium tuberculosis* (Khader et al., 2007), *Klebsiella pneumoniae* (Ye et al., 2001) and *Bordetella pertussis* (Higgins et al., 2006).

Potentiating effects of IL-1β on the expansion and differentiation of different T cell subsets, in particular Th17 cells (Sutton et al., 2006; Acosta-Rodriguez et al., 2007; Dunne et al., 2010; Shaw et al., 2012) have been firmly established. Among T cell subsets, Th17 cells express the highest levels of the IL-1R and IL-1 plays an important role in Th17 priming. Controlled agonistic IL-1 activity could therefore have applications in different physiological/pathological processes, where immunostimulatory effects would be desirable. One of the main concerns regarding the use of IL-1 in immunostimulatory therapies is however its severe toxicity when administered systemically. Thus, when IL-1 action could be confined to a selected cellular population, the toxicity issue might be resolved, which opens up therapeutic perspectives, e.g. for the use as a T-cell adjuvant to enhance the response to weak vaccines (Ben-Sasson et al., 2011). To specifically target IL-1 mutants to the Th17 cell population, IL-1 variants are used that consist of mutant IL-1 fused to a CCL20 targeting moiety. Because activation will be confined to CCR6-expressing cells (ie Th17 cells) only, no major systemic toxicity is expected.

TNFα/Leptin Mutant

TNFα is a cytokine with a wide range of biological activities including cytotoxicity, regulation of immune cells and mediation of inflammatory responses. It is a self-assembling, non-covalently bound, homotrimeric type II transmembrane protein of 233 amino acids. TNFα is active as a membrane-bound as well as a soluble protein, released from the cell membrane after proteolytic cleavage of the 76 aminoterminal amino acids (presequence) by TNFα converting enzyme (TACE, also called ADAM17). It signals through 2 distinct receptors, TNF-R1 (p55) and TNF-R2 (p75), both transmembrane glycoproteins with a cystein-rich motif in the ligand-binding extracellular domain. Despite the extracellular homology, they have distinct intracellular domains and therefore signal different TNF activities (Hehlgans & Pfeffer, 2005). We generated a single chain variant (scTNF) that consists of three TNF monomers coupled via GGGGS-linkers as described before by Boschert et al., 2010.

Leptin is a 16kDa adipocytic cytokine involved in a multitude of biological processes, including immunity, reproduction, linear growth, glucose homeostasis, bone metabolism and fat oxidation, but is best known for its dramatic effect as a satiety signal (Halaas et al., 1995). Because of its effect on immune cells, leptin is also implicated in several auto-immune diseases (Iikuni et al., 2008). Selective targeting of leptin activity may be beneficial for both metabolic and immune- or inflammation-related disorders.

A first aspect of the invention is a fusion protein, comprising at least two cytokines, of which at least one cytokine is a modified cytokine that shows a strongly reduced binding activity towards its receptor, or towards at least one of its receptors, if binding on different receptors is possible. A reduced binding affinity, as used here, means that the affinity is less than 50%, preferably less than 40%, more preferably less than 30%, more preferably more than 25%, more preferably less than 20%, more preferably less than 15%, more preferably less than 10%, more preferably less than 5%, most preferably less than 1% of the wild type cytokine. "Wild type cytokine" as used here, means the cytokine as it occurs in nature, in the host organism. The modification of the cytokine resulting in a reduction in binding affinity can be a modification that decreases the activity of the normal wild type cytokine, or it can be a modification that increases the affinity of a homologous, non-endogenous cytokine (such as, but not limited to a mouse cytokine, binding to a human cytokine receptor). Modifications can be any modification reducing or increasing the activity, known to the person skilled in the art, including but not limited to chemical and/or enzymatic modifications such as pegylation and glycosylation, fusion to other proteins and mutations. Preferably, the cytokine with reduced binding affinity to the receptor is a mutant cytokine. The mutation may be any mutation known to the person skilled in the art, including deletions, insertions, truncations or point mutations. Preferably, said mutation is a point mutation or a combination of point mutations. The affinity can be measured with any method known to the person skilled in the art. As a non-limiting example, the affinity of the ligand towards the receptor can be measured by Scatchard plot analysis and computer-fitting of binding data (e.g. Scatchard, 1949) or by reflectometric interference spectroscopy under flow through conditions, as described by Brecht et al. (1993).

Alternatively, the reduced binding activity can be measured as reduction of the biological activity of the mutant ligand compared to the wild type ligand. In a preferred embodiment, said biological activity is measured in vitro, using a reporter assay. Such reporter assays depend upon the cytokine receptor system used, and are known to the person skilled in the art. As a non-limiting example, an IFN-γ reporter assay is described by Bono et al (1989) together with the Scatchard analysis. Preferably the biological activity of the mutant is less than 50%, preferably less than 40%, more preferably less than 30%, more preferably more than 25%, more preferably less than 20%, more preferably less than 15%, more preferably less than 10%, more preferably less than 5%, most preferably less than 1% of the wild type cytokine The modified cytokine is fused to another cytokine, modified or not. Preferably, both cytokines are fused using a linker sequence, preferably a GGS linker, comprising one or more GGS repeats. The modified cytokine may be placed in the aminoterminal part of the molecule, or in the carboxyteminal part; the fusion protein may further comprise other domains such as, but not limited to a tag sequence, a signal sequence, another cytokine or an antibody.

A cytokine as used here may be any cytokine known to the person skilled in the art, including, but not limited to cytokines of the α-helical bundle cytokine family, the trimeric tumor necrosis factor (TNF) family (Idriss and Naismith, 2000), the cysteine knot growth factors (Sun and Davies, 1995), the β-trefoil fold group that includes the interleukin-1 family (Murzin et al., 1992), the interleukin 17 (IL-17) family (Gaffen, 2011), and the chemokines (Nomiyama et al., 2013). In case of a member of the trimeric TNF family, preferably a single chain version is used. Such single chain cytokines are known to the person skilled in the art, and are described, amongst others, by Krippner-Heidenrich et al. (2008)

In one preferred embodiment, said fusion protein is a fusion between XCL1 and a IFNα2-mutant, preferably a Q124R mutant. In another preferred embodiment, said fusion is a fusion between CCL20 and an IL1β mutant. Preferably, said IL1β mutant is a Q148G mutant. In still another preferred embodiment, said fusion is a fusion between TNFα and a leptin mutant. Preferably, said leptin mutant is a selected from the group consisting of L86S and L86N.

Another aspect of the invention is a fusion protein according to the invention for use as a medicament. In one preferred embodiment it is a fusion protein according to the invention for use in treatment of cancer. In another preferred embodiment, it is a fusion protein according to the invention for use in modulation of the immune response.

STAT1 Y701 phosphorylation is measured in response to IFNα/β or XCL1/IFNα2-Q124R fusion protein in different mouse splenocyte subsets, characterized by the expression of CD11c and CD8α. First column: $CD11c^-$ $CD8\alpha^+$ subset; second column: $CD11c^-$ $CD8\alpha^-$ subset; third column: $CD11c^{medium}$ $CD8\alpha^-$ subset; fourth column: $CD11c^{high}$ $CD8\alpha^+$ subset; fifth column: $CD11c^{high}$ $CD8\alpha^-$ subset.

Figure 3:
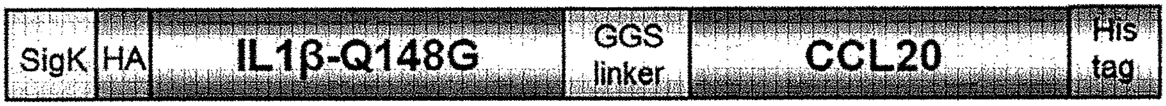

FIG. 3: Schematic representation of the structural elements in the IL-1β-mutant/CCL20 fusion proteins.

Figure 4:
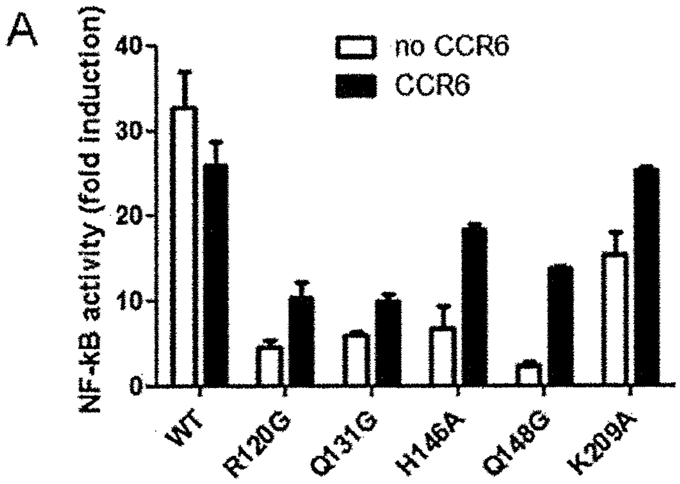
Figure 4:
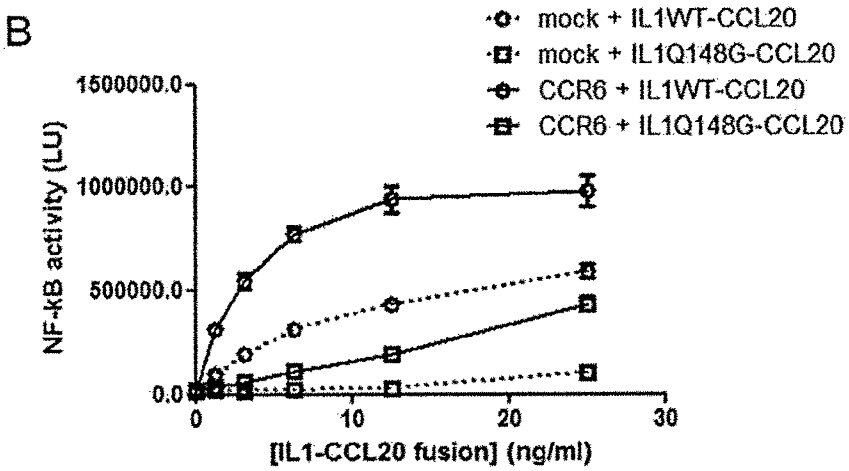
Figure 4:
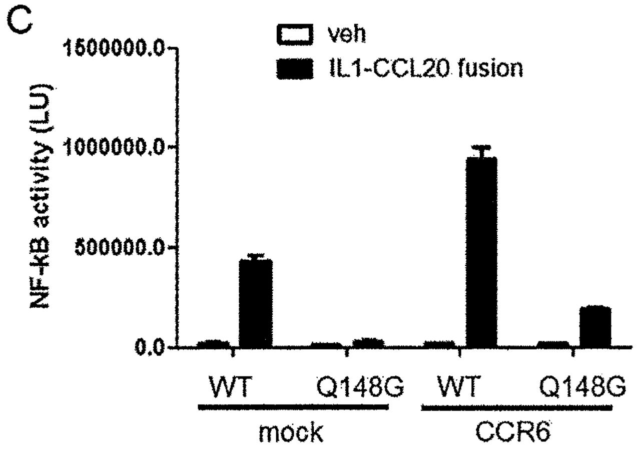

FIG. 4: Selective activity of the IL-1β-mutant/CCL20 fusion proteins on CCR6 expressing cells.

(A) induction of NFκB activity by wild type and 5 different IL-1β mutants, fused to CCL20.

(B) concentration dependency of the induction of the NFκB activity by wild type and IL-1β Q148G mutant/CCL20 fusion proteins, in mock transfected cells, or cells transfected with CCR6.

(C) induction of the NFκB activity by wild type and IL-1β Q148G mutant/CCL20 fusion proteins (12.5 ng/ml), in mock transfected cells, or cells transfected with CCR6 as compared with induction by vehicle.

Figure 5:

FIG. 5: Schematic representation of the structural elements in the scTNFα/Leptin-mutant fusion proteins.

Figure 6:
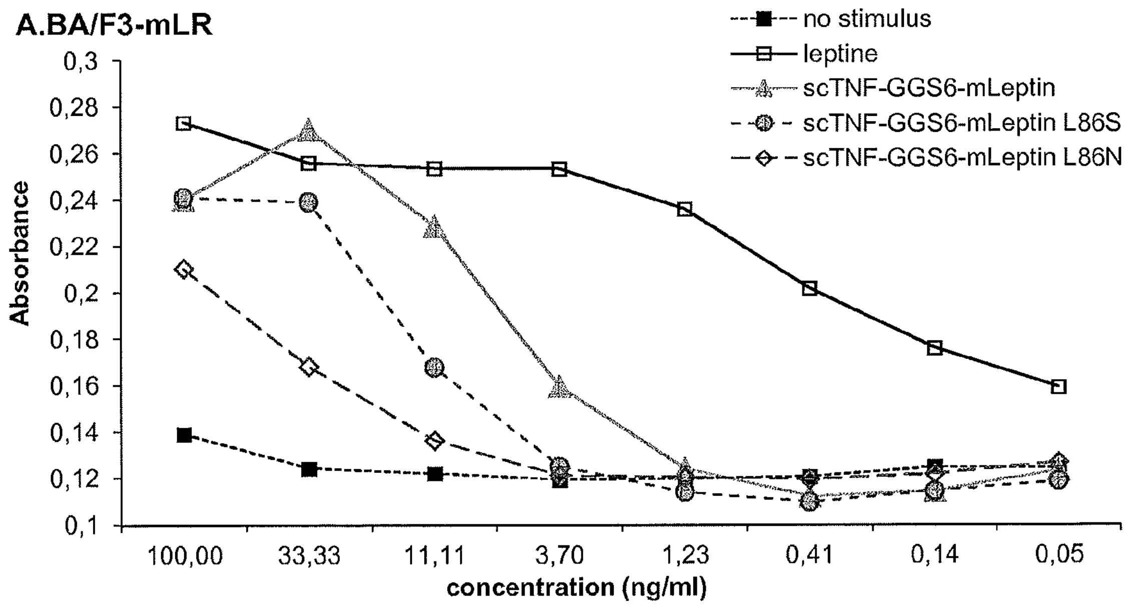
Figure 6:
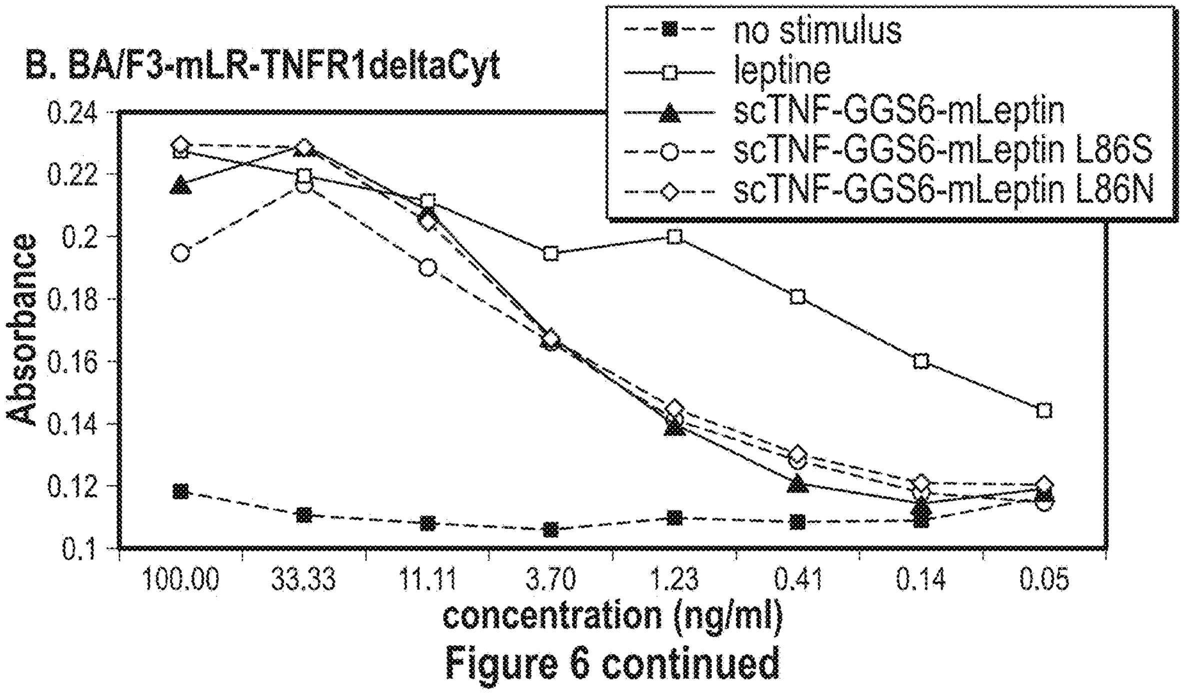

FIG. 6: Selective activity of the scTNFα/Leptin mutant fusion proteins on leptin receptor expressing cells.

Leptin-dependent growth induced by indicated concentrations of scTNF-targeted WT or mutant leptin is measured by the XTT assay in Ba/F3-mLR cells (panel A) or Ba/F3-mLR-TNFR1ΔCyt cells (panel B).

Figure 7:
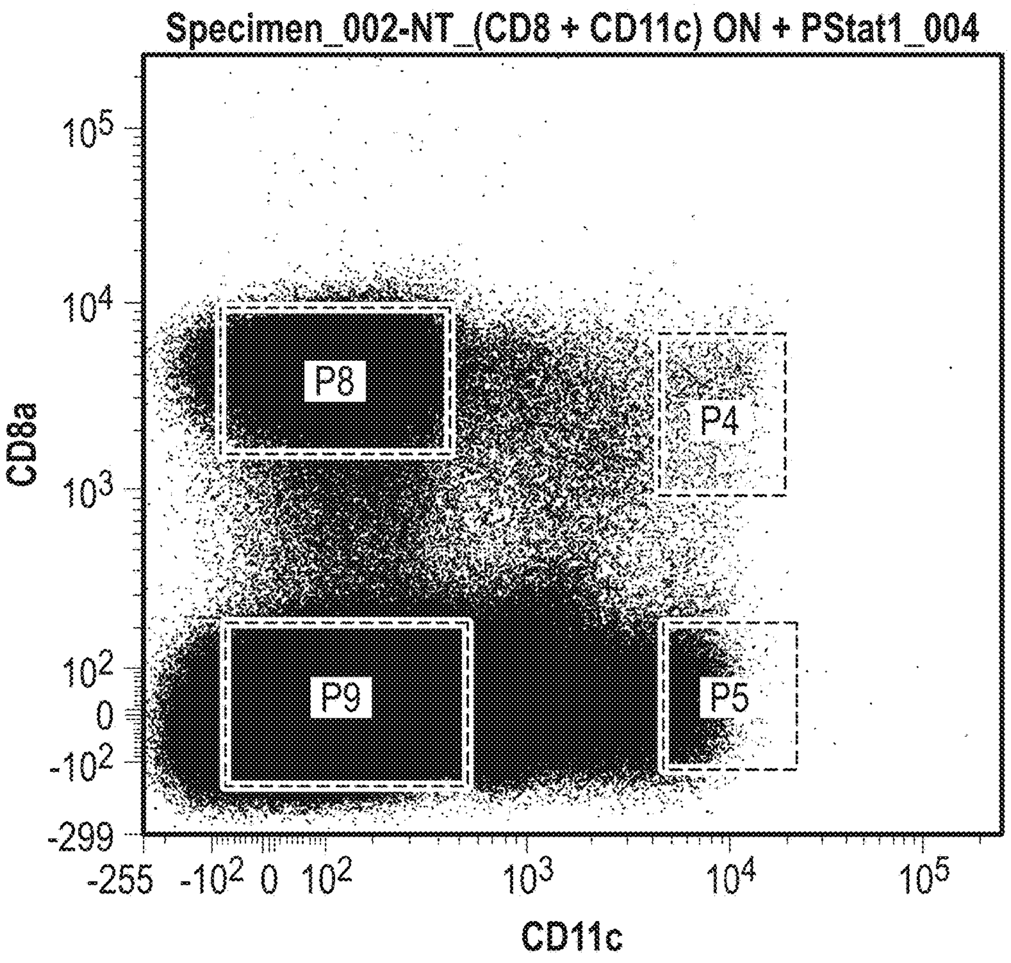
Figure 7:
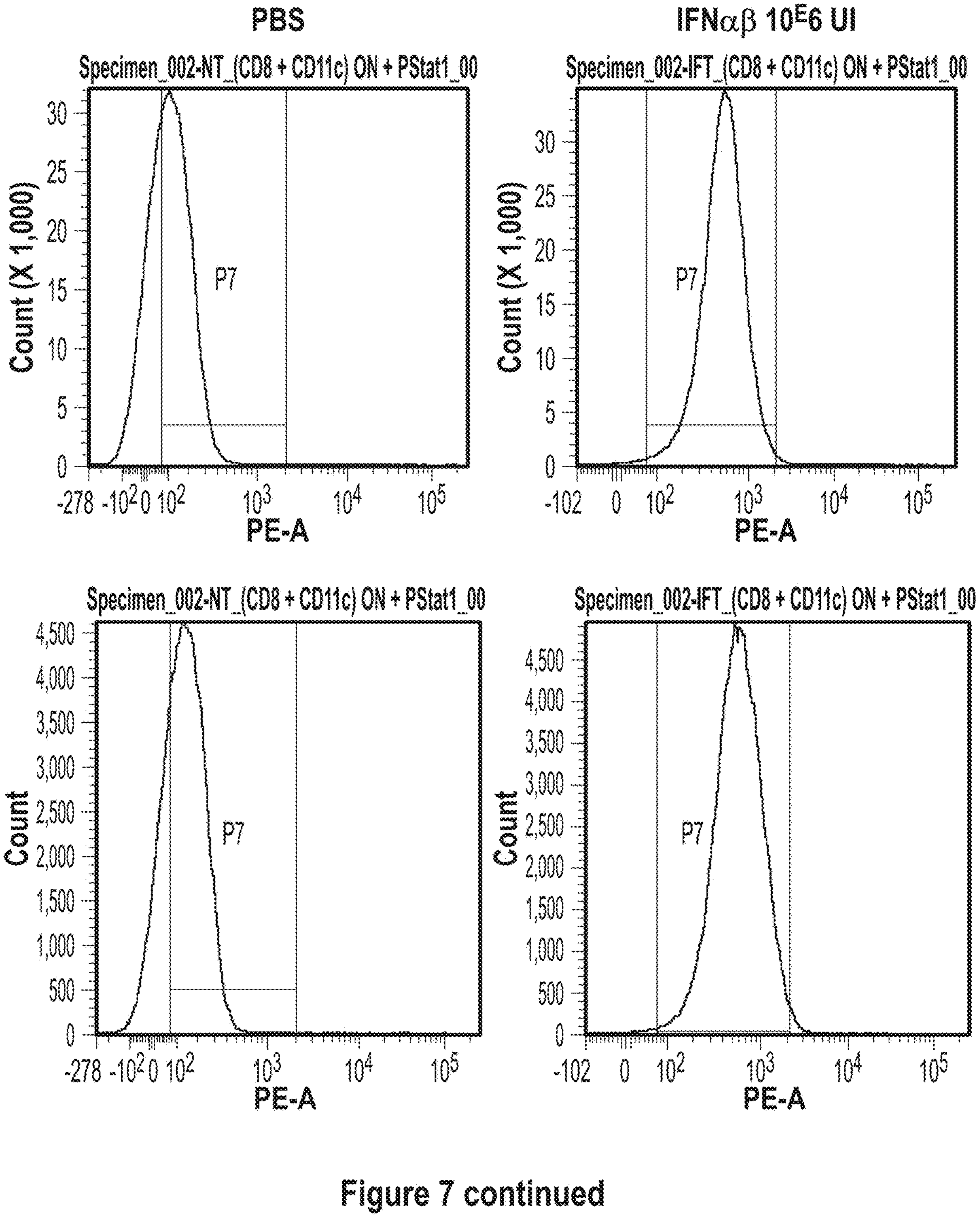
Figure 7:
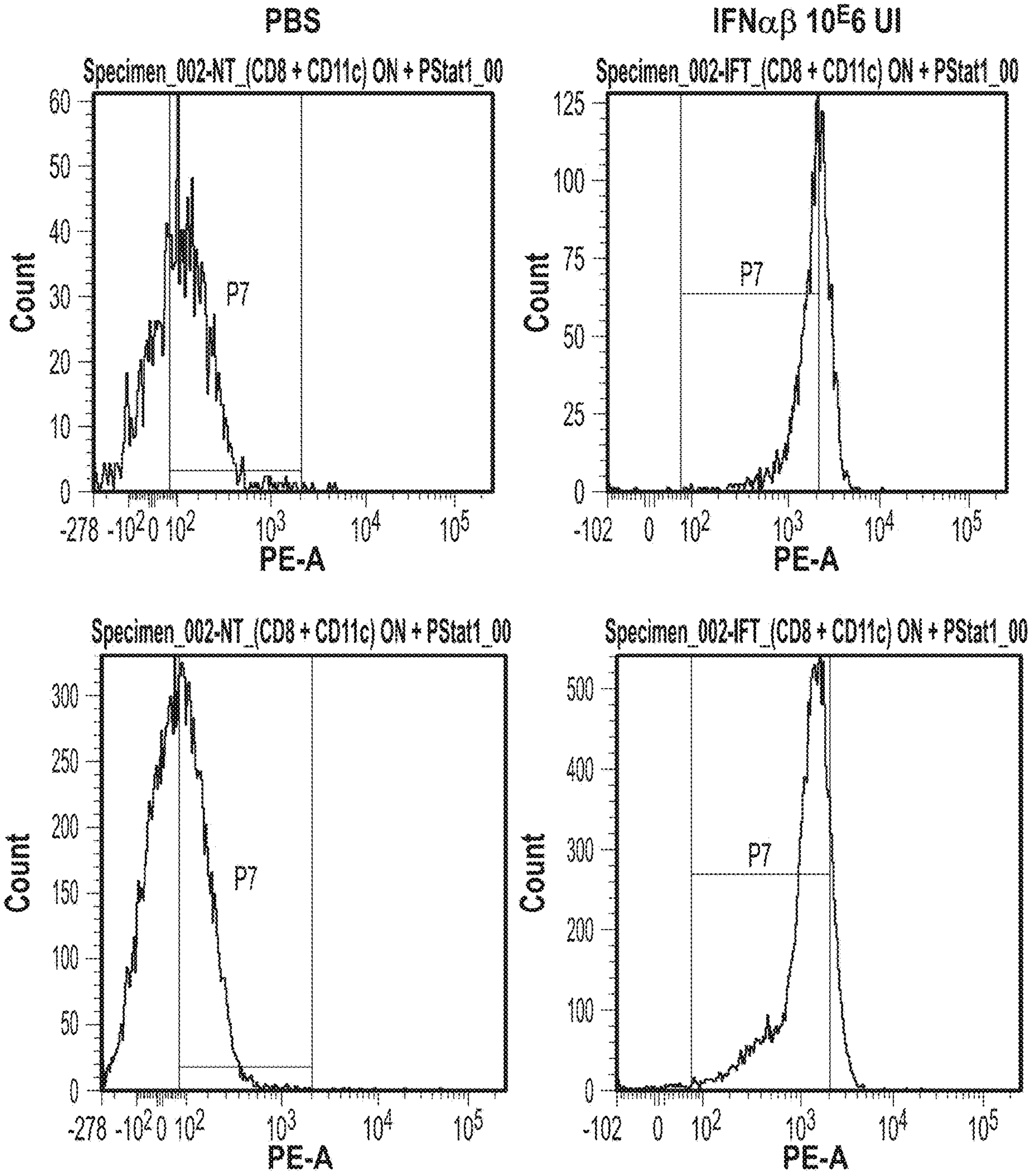
Figure 7:
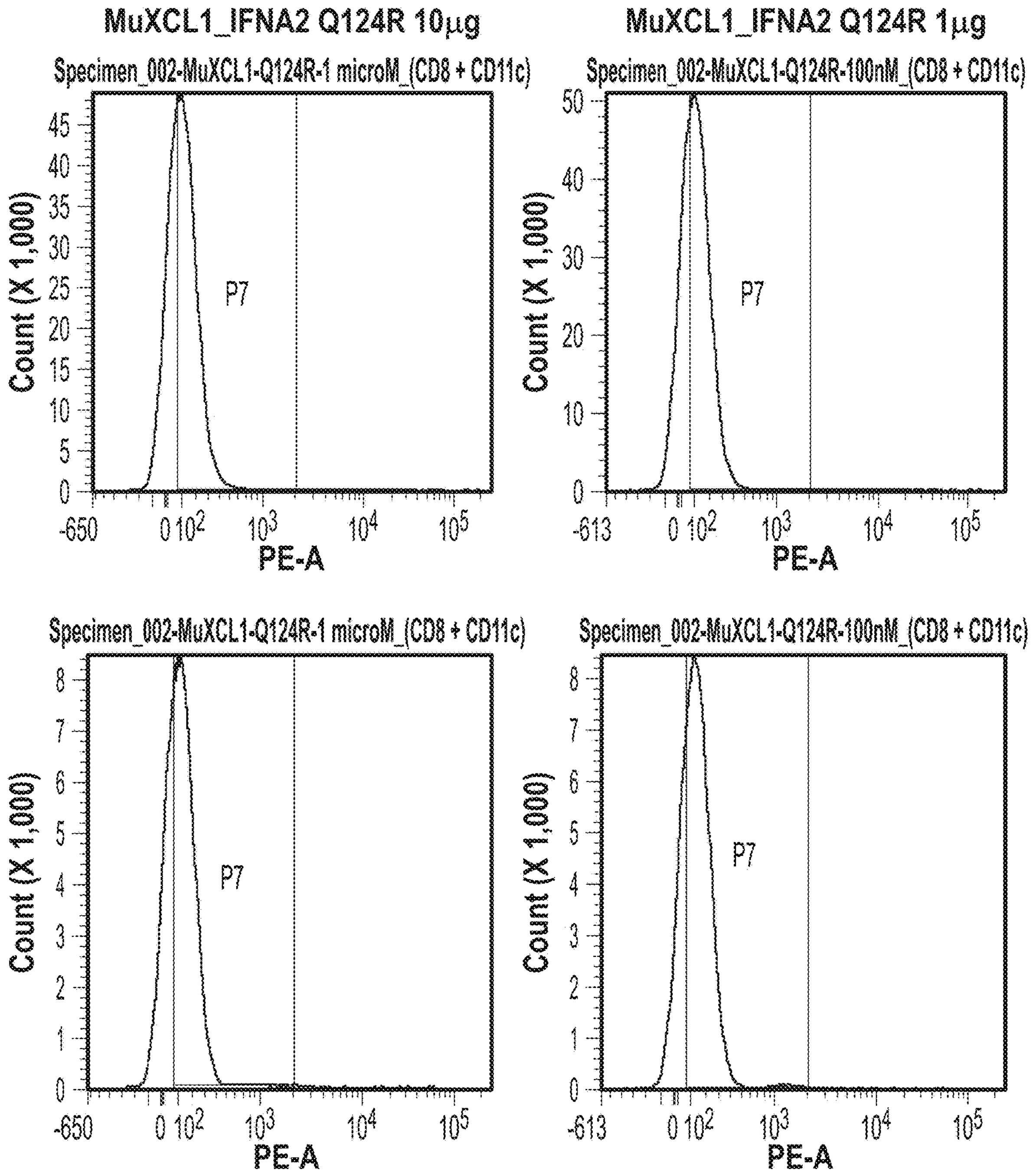
Figure 7:
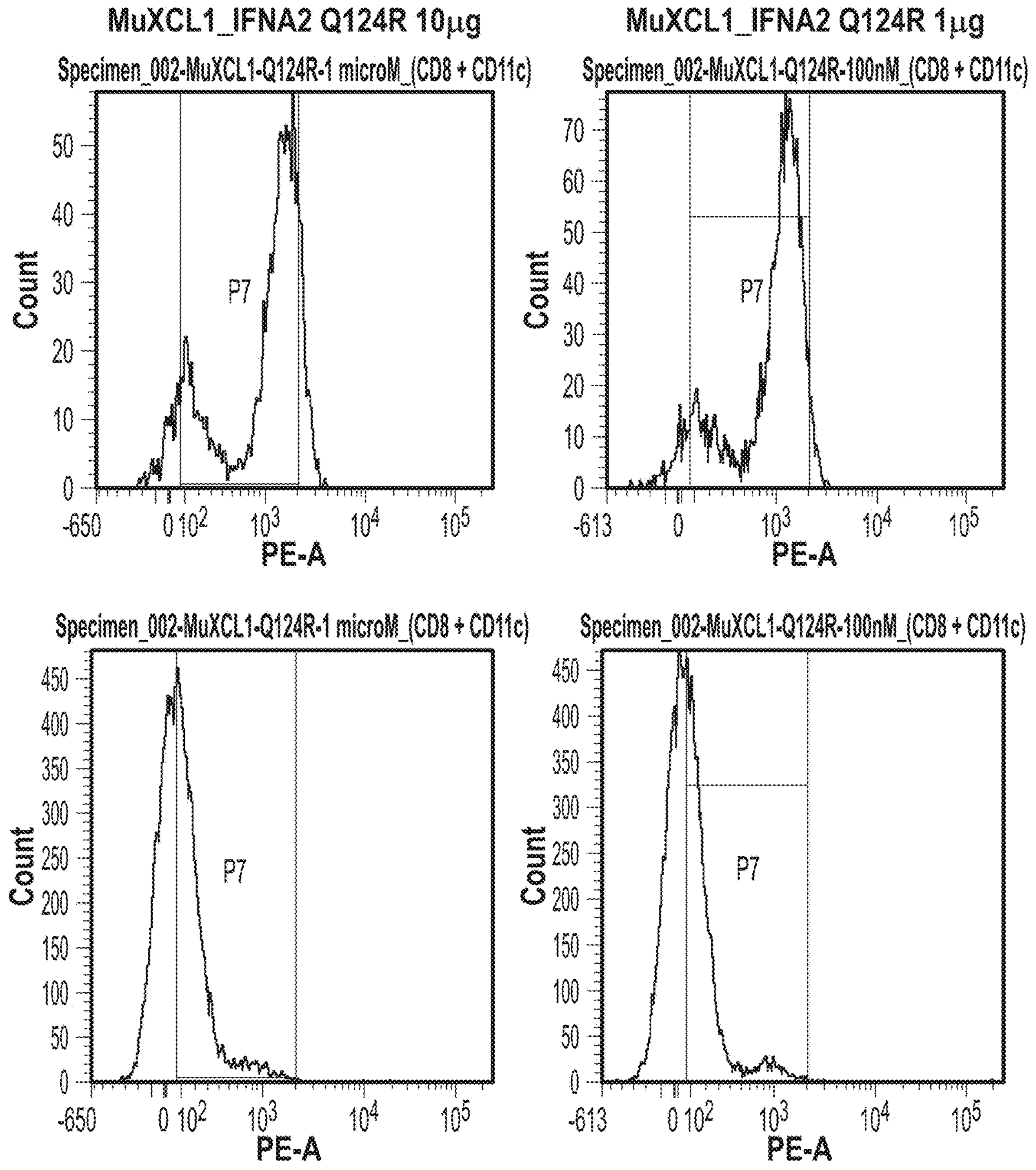
Figure 7:
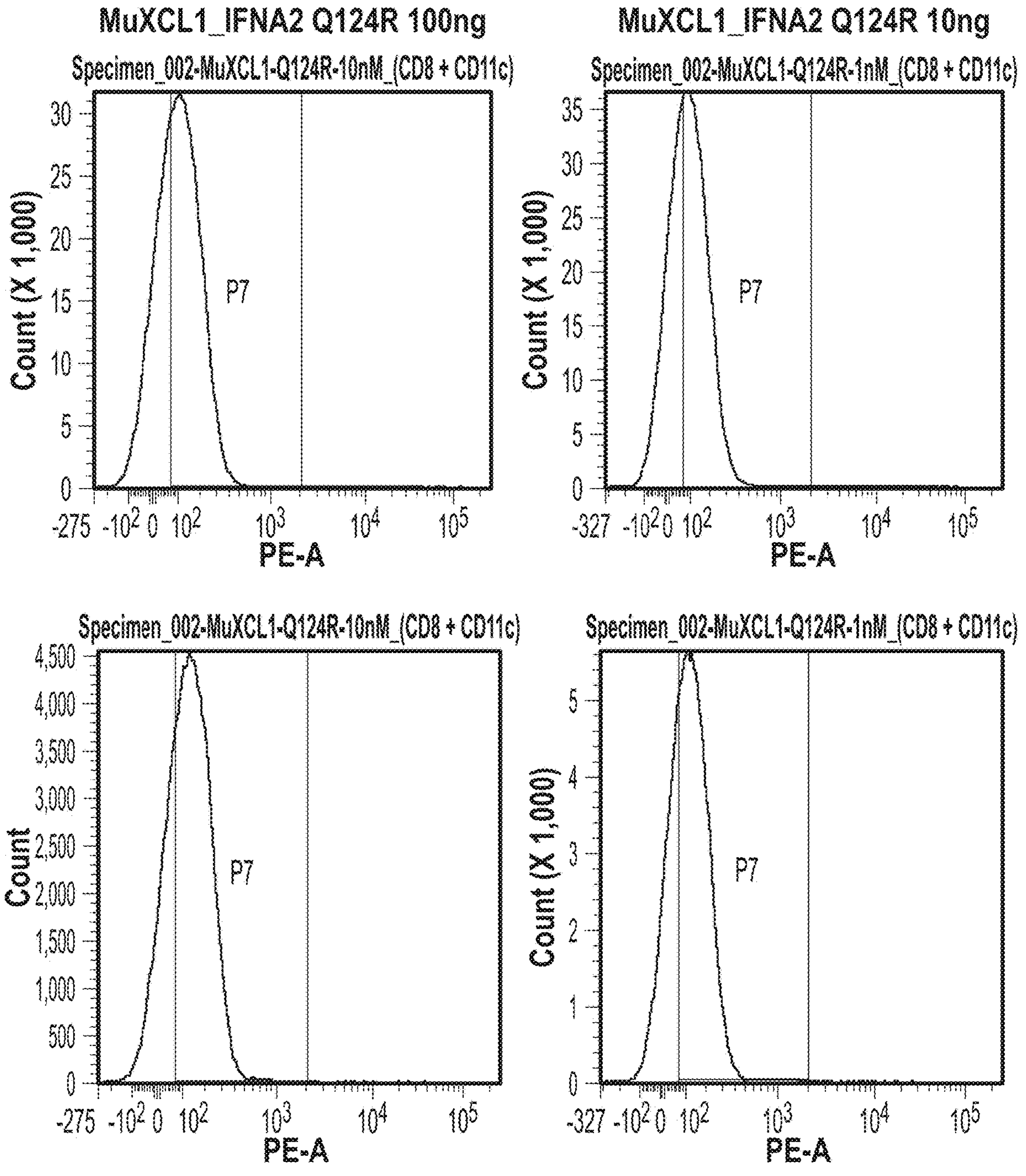
Figure 7:
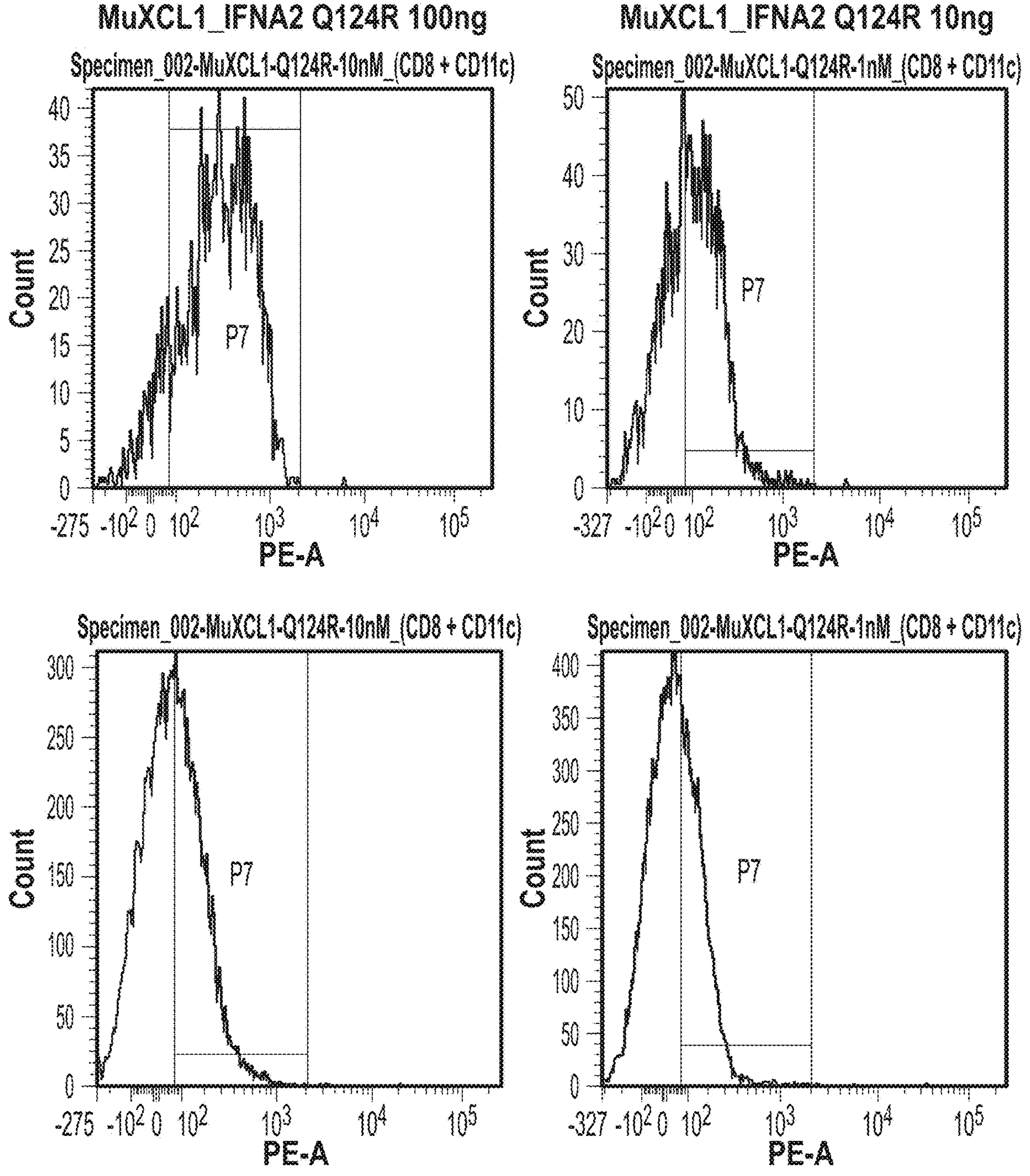

FIG. 7: In vivo targeting of IFN activity on mouse spleen cells expressing XCR1.

C57Bl/6 mice were injected iv with the indicated amount of XCL1-IFNα2-Q124R or with 1 000 000 units of natural murine IFNα/β or PBS. After 45 min, spleen cells were analyzed by FACS for CD11c and CD8α expression (first panel) and for P-STAT1 (further panels) in the following cell population: CD11c−CD8α− (line 1), CD11c−CD8α+ (line 2), CD11c+CD8α+ (line3), CD11c+CD8α− (line 4).

EXAMPLES

Materials & Methods to the Examples

Cloning and Production of the Fusokines

Cloning of the XCL1/IFNα2-Q124R Fusion Protein.

The XCL1 open reading frame was synthesized by PCR from the XCL1-encoding plasmid MR200473 (Origen Inc.), using the Expand High Fidelity PCR system (Roche Diagnostics) and the following primers:

```
Forward: 5'GGGGGGGAATTCATGAGACTTCTCCTCCTGAC3'

Reverse: 5'GGGGGGTCCGGAGGCCCAGTCAGGGTTATCGCTG3'
```

The PCR product was digested by EcoRI and BspEI and substituted to the EcoRI-BspEI fragment which encodes the nanobody in the pMET7 SIgK-HA-1R59B-His-PAS-ybbr-IFNA2-Q124R vector (PCT/EP2013/050787).

Production of the XCL1/IFNα2-Q124R Fusion Protein.

Hek 293T cells were transfected with the protein fusion construct using the standard lipofectamin method (Invitrogen). 48 hours after the transfection culture medium were harvested and stored at −20° C. The IFN activity was assayed on the human HL116 and the murine LL171 cell lines as described (Uzé et al. J. Mol. Biol. 1994) using the purified Nanobody GFP-IFNα2-Q124R preparation (described in PCT/EP2013/050787) as a standard.

Cloning of IL-1β/CCL20 Fusion Proteins.

A codon-optimized sequence encoding the mature human IL-16/CCL20 fusion protein was generated via gene synthesis (Invitrogen Gene Art). Briefly, a sequence was synthesized in which the mature human IL-1β protein, preceded by the SigK leader peptide, and equipped with an N-terminal HA, was fused at its C-terminus to a 13×GGS linker sequence, followed by the sequence for mature human CCL20 with a C-terminal HIS tag (FIG. 3).

IL-1β mutants expected to have reduced binding affinity for the IL-1R were selected based on literature and analysis of published crystal structures of human IL-1β complexed with its receptor. Mutations in the hIL-1β moiety were created via site-directed mutagenesis (QuickChange, Stratagene) using the mutagenesis primers as indicated in the table:

| | Fw primer | Rev primer |
|---|---|---|
| R120G | GCGGCAGCGCCCCTGTCGGA AGCTTGAACTGCACCCTGC | GCAGGGTGCAGTTCAAGCTT CCGACAGGGGCGCTGCCGC |
| Q131G | CTGCGGGACAGCCAGGGGA AGAGCCTGGTCATGAGCG | CGCTCATGACCAGGCTCTTC CCCTGGCTGTCCCGCAG |
| H146A | CGAGCTGAAGGCACTGGCT CTTCAGGGCCAGGACATGG | CCATGTCCTGGCCCTGAAGA GCCAGTGCCTTCAGCTCG |
| Q148G | GAAGGCACTGCATCTGGGT GGCCAGGACATGGAACAGC | GCTGTTCCATGTCCTGGCCA CCCAGATGCAGTGCCTTC |
| K209A | CCCCAAGAACTACCCCAAG GCAAAGATGGAAAAGCGCT TCGTGTTCAAC | GTTGAACACGAAGCGCTTTT CCATCTTTGCCTTGGGGTAG TTCTTGGGG |

Production of IL-1β-mutant: CCL20 Fusion Proteins.

IL-1β-CCL20 fusion proteins were produced in HEK293T cells. For small-scale production, HEK293T cells were seeded in 6-well plates at 400000 cells/well in DMEM supplemented with 10% FCS. After 24 hours, culture medium was replaced by medium with reduced serum (DMEM/5% FCS) and cells were transfected using linear PEI. Briefly, PEI transfection mix was prepared by combining 1 μg expression vector with 5 μg PEI in 160 μl DMEM, incubated for 10 minutes at RT and added to the wells dropwise. After 24 hours, transfected cells were washed with DMEM and layered with 1.5 ml OptiMem/well for protein production. Conditioned media were recuperated after 48 hours, filtered through 0.45μ filters and stored at −20° C. IL-1β content in the conditioned media was determined by ELISA according to the manufacturer's instructions (R&D Systems).

Cloning of the scTNF/Leptin Fusion Proteins.

The coding sequences of the wild-type (WT), L86S and L86N leptin were synthesized by PCR from pMet7 plasmids expressing WT Leptin, Leptin L86S or Leptin L86N, respectively, using the following primers:

```
forward 5'-GCAGATCTGTCGACATCCAGAAAGTCCA
           GGATGACACC-3',

reverse 5'-CGATGCGGCCGCACATTCAGGGCTAACA
           TCCAACTGT-3'.
```

This introduces a BglII and a NotI site at the amino and carboxy terminus, respectively, of the leptin coding sequence. The PCR product was digested with BglII and NotI and cloned into pMET7-SIgK-HA-scTNF WT-6× GGS-FLAG (WT scTNF was generated by gene synthesis, GeneArt) opened with BglII and NotI, which reside in between the 6×GGS and FLAG. This generated pMET7-SIgK-HA-scTNF WT-6×GGS-mLeptin-FLAG, pMET7-SIgK-HA-scTNF WT-6×GGS-m Leptin L86S-FLAG and pMET7-SIgK-HA-scTNF WT-6×GGS-mLeptin L86N-FLAG.

Production of the scTNF/Leptin Fusion Proteins.

HekT cells were transfected with the different fusion protein constructs using the standard calcium phosphate precipitation method. 48 hours after the transfection culture mediums were harvested and stored at −20° C. The concentration was determined with a commercial hTNFα ELISA (DY210, R&D systems).

Cell Lines

Hek 293T, HL116 and LL171 cell line were grown in DMEM supplemented with 10% FCS. Ba/F3-mLR and Ba/F3-mLR-TNFR1ΔCyt cells were maintained in RPMI supplemented with 10% heat-inactivated FCS and 100 ng/ml leptin.

Assays

Phospho STAT1 Assay.

Single-cell suspensions were prepared from spleens isolated from C57Bl/6 mice. Erythrocytes were depleted using red blood cell lysis buffer (Lonza). Splenocytes were treated for 30 min with mouse IFNα/β or XCL1-IFNα2-Q124R fusion protein in RPMI 5% fetal calf serum at 37° C. and then labelled with the BD Phosflow PE mouse anti-STAT1 (pY701) together with the Alexa Fluor 488-labelled anti-mouse CD11c (eBioscience #53-0114-80) and APC-labelled anti mouse CD8α (BD Bioscience #553035) or anti-mouse CD11c and Alexa 488-labelled anti-mouse CD8α according to BD Biosciences instructions. FACS data were acquired using a BD FACS Canto and analyzed using either Diva (BD Biosciences) software.

NF-κB Reportergene Assay.

To assess IL-1R activation, we used HEK-Blue™ IL-18 cells that stably express the IL-1R (Invivogen) and transfected them transiently with an NF-κB luciferase reportergene. Briefly, HEK-Blue™ IL-1β cells were seeded in culture medium (DMEM/10% FCS) in 96-well plates (10000 cells/well) and transfected the next day using the calciumphosphate precipitation method with the indicated amounts of expression plasmids and 5 ng/well of the 3κB-Luc reportergene plasmid (Vanden Berghe et al., 1998). 24 hours post-transfection, culture medium was replaced by starvation medium (DMEM) and 48 hours post-transfection, cells were induced for 6 hours with IL1-CCL20 fusion proteins. After induction, cells were lysed and luciferase activity in lysates was determined using the Promega Firefly Luciferase Assay System on a Berthold centro LB960 luminometer.

Cell Proliferation Assay.

The Ba/F3-mLR cell line was generated by electroporation of Ba/F3 cells with the pMet7-mLR vector. Stably expressing cells were selected by growing them on leptin instead of IL-3. Indeed, growth of Ba/F3 cells is dependent on IL-3, but when they express mLR, they also proliferate with leptin. To obtain the Ba/F3-mLR-TNFR1ΔCyt cell line, Ba/F3-mLR cells were co-transfected with pMet7-HA-hTNFR1ΔCyt and pIRESpuro2 (Clontech) followed by puromycin selection and FACS sorting of hTNFR1ΔCyt-expressing cells.

To assess cell proliferation, Ba/F3-mLR and Ba/F3-mLR-TNFR1ΔCyt cells were washed, seeded in RPMI/10% IFCS in 96-well plates (10.000 cells/well) and stimulated with the indicated amounts of leptin or fusion proteins. Four days later, 50 ul XTT (XTT Cell Proliferation Kit II, Roche, 11 465 015 001) was added and incubated for 4 hrs before measuring absorbance at 450 nm.

Example 1

IFN Activity of the XCL1/IFNα2-Q124R Fusion Protein is Restored on Cells Expressing XCR1

Figure 1:
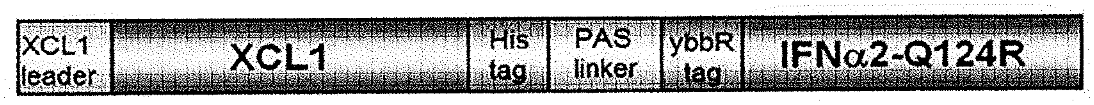
FIG. 1: Schematic representation of the structural elements in the XCL1/IFNα2-Q124R fusion protein.
Figure 2:
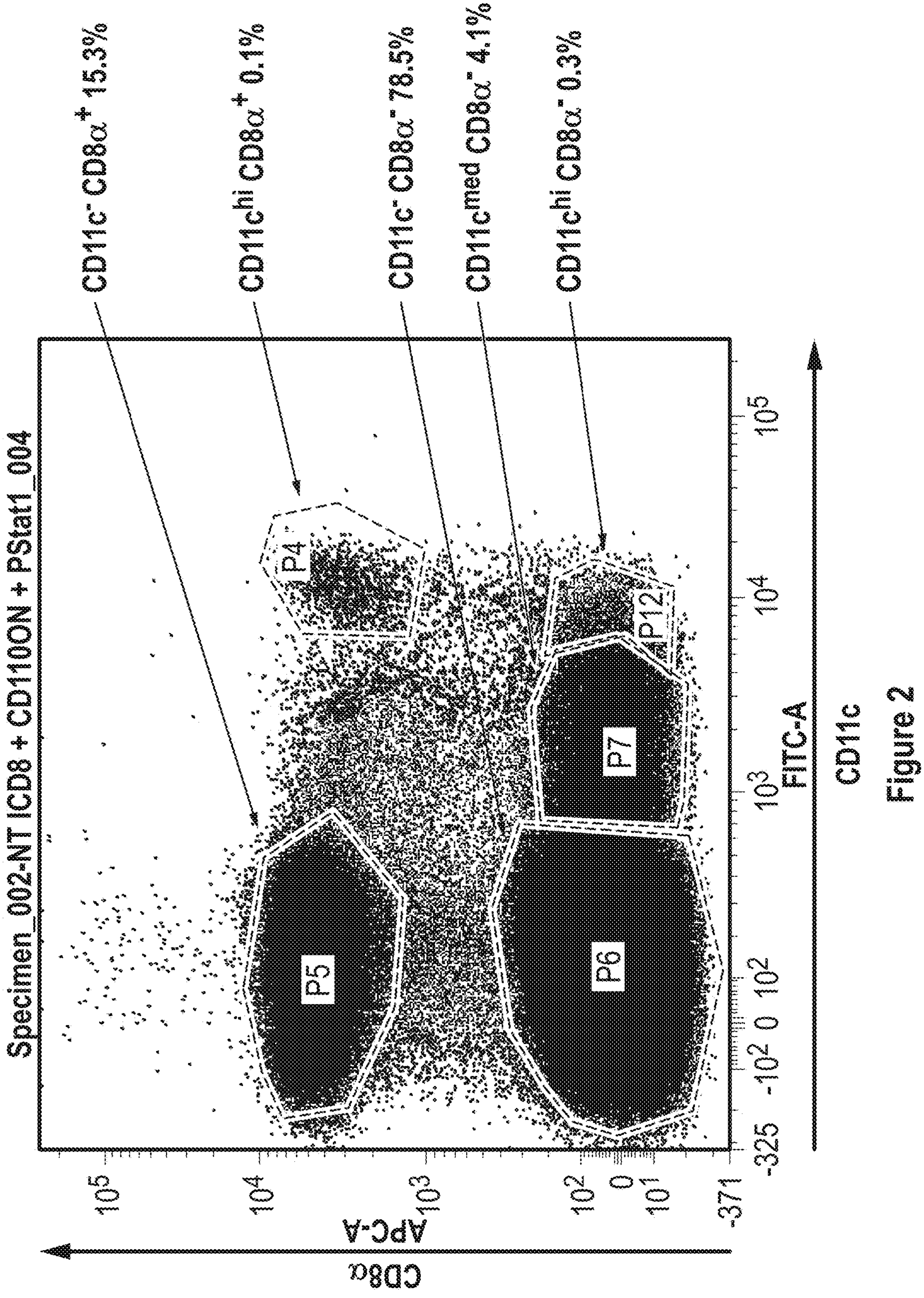
FIG. 2: Selective activity of the XCL1/IFNα2-Q124R fusion protein on XCR1 expressing cells.
Figure 2:
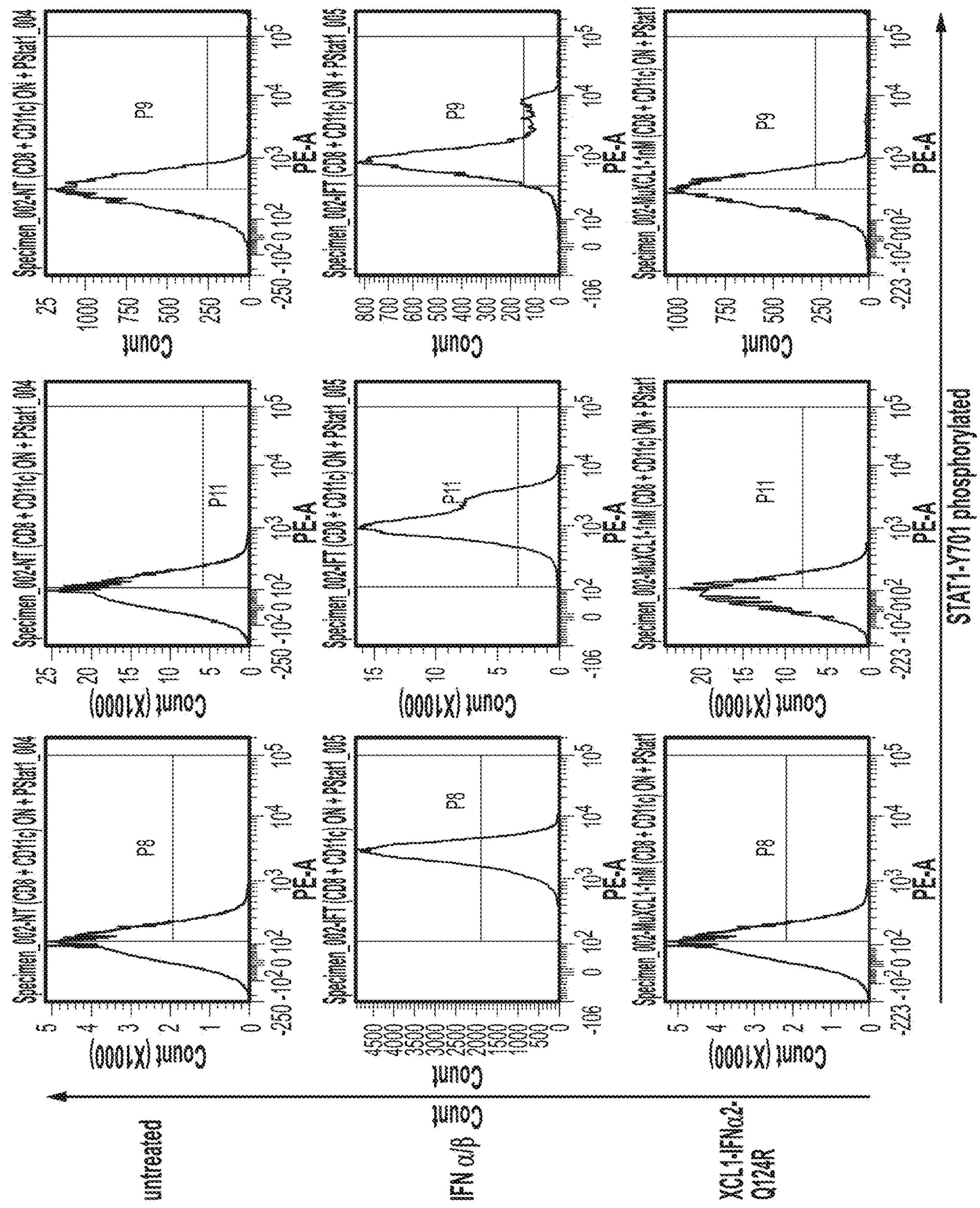
Figure 2:
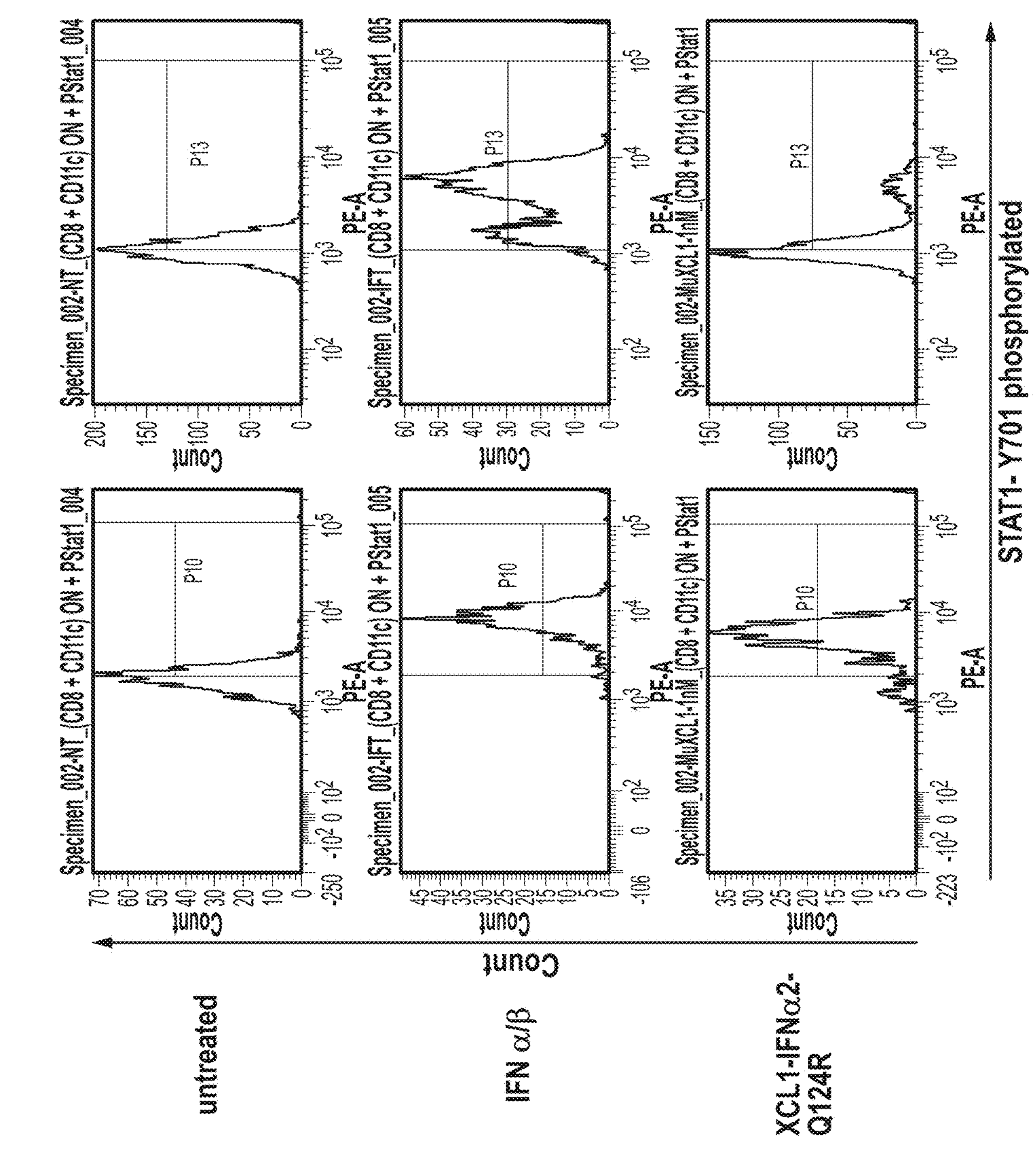

Mouse splenocytes were treated for 30 minutes with 1 nM XCL1-IFNα2-0124R or with 10000 units/ml mouse IFNα/β. Cells were then fixed, permeabilized and stained with an anti-phospho STAT1 (PE), anti CD11c (Alexa Fluor 488) and anti CD8α (APC) and analyzed by FACS. FIG. 2 shows that mouse IFN α/β induced STAT1 phosphorylation in all splenocyte subsets analysed. In contrast the XCL1-IFNα2-Q124R fusion protein induced an IFN response only in the majority of cells belonging to the CD11c$^+$ CD8α$^+$ subset and in a minority of cells belonging to the CD11c$^+$ CD8α$^-$ subset. The distribution of the splenocyte subsets responding to the XCL1-IFNα2-Q124R fusion protein matches perfectly the expected distribution of XCR1, the XCL1 receptor (Dorner et al. 2009).

Example 2

IL1β Activity is Restored on Cells Expressing CCR6

HEK-Blue™ IL-1β cells, which stably express the IL-1R, were transiently transfected with an NF-κB reportergene plasmid (5 ng/well) and an empty vector or hCCR6 expression plasmid (10 ng/well). Mock- and CCR6-transfected cells were next treated for 6 hours with wild type or mutant IL1β-CCL20 fusion proteins (25 ng/ml), after which cells were lysed and NF-κB reportergene activity was determined. As evident from FIG. 4A, cells expressing CCR6 responded with increased NF-κB reportergene activity to all investigated mutant IL1β-CCL20 fusion proteins as compared to mock-transfected cells. To evaluate the effect of the IL-1β-Q148G mutant, for which the targeting effect was most apparent, in more detail, mock-transfected or CCR6-expressing HEK-Blue™ IL-1β cells were treated for 6 hours with increasing doses of WT IL-1β or IL-1βQ148G-CCL20 fusion protein. FIG. 4B demonstrates that overexpression of CCR6 increased the activity of the WT IL-1β-CCL20 fusion, but had a stronger potentiating effect for the IL-1βQ148G-CCL20 fusion. The targeting effect was most prominent when IL1-β-CCL20 was applied to the cells at 12.5 ng/ml (FIG. 4C).

Example 3

Leptin Activity is Restored on Cells Expressing the TNFR

The proliferation of Ba/F3-mLR and Ba/F3-mLR-TNFR1ΔCyt cells after 4 days of stimulation with the indicated amounts of leptin or the leptin-scTNF fusion proteins was assessed. As shown in FIG. 6A, both cell lines do not proliferate in growth medium supplemented only with heat-inactivated serum. Moreover, the ability of leptin to induce Ba/F3 proliferation is reduced when it is coupled to scTNF. Mutating L86 within WT leptin into either a serine (L86S) or an asparagine (L86N) results in a moderate or a strong reduction of the affinity towards the mouse leptin receptor, respectively. This reduction in affinity translates in a 3 versus 10 times less potent induction of proliferation of Ba/F3-mLR cells for leptin L86S versus L86N, respectively. Additional transfection of Ba/F3-mLR cells with the human TNF-R1 lacking its intracellular domain (hTNFR1ΔCyt) introduces a non-functional receptor, which can function as a membrane bound extracellular marker. Clearly, the proliferative response upon stimulation with the L86S and L86N leptin mutants coupled to scTNF is completely restored in Ba/F3-mLR cells that express the hTNFR1ΔCyt (FIG. 6B).

Example 4

In Vivo Targeting of an XCR1 Expressing Cell Population

According to Bachem et al. (Frontiers in Immunology 3, 1-12. 2012), XCR1 expressing cells represent the major part of CD11c+ CD8α+ spleen cell population and a minor part of CD11c+ CD8α− spleen cell population. C57Bl/6 mice were injected iv with the indicated amount of XCL1-IFNα2-Q124R or with 1 000 000 units of natural murine IFNα/β or PBS. After 45 min, spleen cells were analyzed by FACS for P-STAT1 in the following cell population: CD11c− CD8α−, CD11c− CD8α+, CD11c+ CD8α+, CD11c+ CD8α−. The results are shown in FIG. 7. From these results, it is clear that the fusion construct can target and induce a response in a minor fraction of the population (about 0.1% of the total cells), whereas the IFN sensitive cells that do not express the marker are not affected. Indeed, wild type IFN is also affecting the CD11c+ CD8α− cells, whereas those cells are not affected by the fusion construct, clearly proving the specific action of the fusion.

REFERENCES

Acosta-Rodriguez E V, Napolitani G, Lanzavecchia A and Sallusto F. (2007) Interleukins 1beta and 6 but not transforming growth factor-beta are essential for the differentiation of interleukin 17-producing human T helper cells. Nat Immunol. 8, 942-9.

Acres B, Gantzer M, Remy C, Futin N, Accart N, Chaloin O, Hoebeke J, Balloul J M and Paul S. (2005). Fusokine interleukin-2/interleukin-18, a novel potent innate and adaptive immune stimulator with decreased toxicity. Cancer Res. 65, 9536-46.

Baba M, Imai T, Nishimura M, Kakizaki M, Takagi S, Hieshima K, Nomiyama H and Yoshie O. (1997). Identification of CCR6, the specific receptor for a novel lymphocyte-directed CC chemokine LARC. J Biol Chem. 272,14893-8.

Bachem A, Hartung E, Güttler S, Mora A, Zhou X, Hegemann A, Plantinga M, Mazzini E, Stoitzner P, Gurka S, Henn V, Mages H W and Kroczek R A. (2012). Expression of XCR1 Characterizes the Bantf3-Dependent Lineage of Dendritic Cells Capable of Antigen Cross-Presentation. Front Immunol. 3, 214. doi: 10.3389.

Ben-Sasson S Z, Caucheteux S, Crank M, Hu-Li J and Paul W E. (2011). IL-1 acts on T cells to enhance the magnitude of in vivo immune responses. Cytokine, 56, 122-5.

Bono M R, Benech P, Coullin P, Alcaide-Loridan C, Grisard M C, Join H, Fischer D G and Fellous M. (1989). Characterization of human IFN-gamma response using somatic cell hybrids of hematopietic and nonhematopoietic origin. Somat. Cell Mol. Genet. 15, 513-23.

Brecht A., Gauglitz G., Polster J. (1993). Interferometric immunoassay in a FIA-system—A sensitive and rapid approach in label-free immunosensing. Biosens Bioelectron 8: 387-392.

Crozat K, Guiton R, Contreras V, Feuillet V, Dutertre C A, Ventre E, Vu Manh T P, Baranek T, Storset A K, Marvel J, Boudinot P, Hosmalin A, Schwartz-Cornil I and Dalod M. (2010). The XC chemokine receptor 1 is a conserved selective marker of mammalian cells homologous to mouse CD8alpha+ dendritic cells. J. Exp. Med. 207, 1283-1292.

Donahue R E, Seehra J, Metzger M, Lefebvre D, Rock B, Carbone S, Nathan D G, Garnick M, Sehgal P K, Laston D, et al. (1988). Human IL-3 and GM-CSF act synergistically in stimulating hematopoiesis in primates. Science 241, 1820-1823

Dorner B G, Dorner M B, Zhou X, Opitz C, Mora A, Guttler S, Hutloff A, Mages H W, Ranke K, Schaefer M, Jack R S, Henn V and Kroczek R A. (2009). Selective expression of the chemokine receptor XCR1 on cross-presenting dendritic cells determines cooperation with CD8+ T cells. Immunity 31, 823-833.

Dunne A, Ross P J, Pospisilova E, Masin J, Meaney A, Sutton C E, Iwakura Y, Tschopp J, Sebo P and Mills K H. (2010) Inflammasome activation by adenylate cyclase toxin directs Th17 responses and protection against *Bordetella pertussis*. J Immunol. 185, 1711-9.

Fuertes M B, Kacha A K, Kline J, Woo S R, Kranz D M, Murphy K M and Gajewski T F (2011). Host type I IFN signals are required for antitumor CD8+ T cell responses through CD8{alpha}+ dendritic cells J. Exp. Med. 208, 2005-2016.

Gaffen S L. (2011). Recent advances in the IL-17 cytokine family. Curr Opin Immunol. 23, 613-9.

Gajewski T F, Fuertes M B and Woo S R (2012). Innate immune sensing of cancer: clues from an identified role for type I IFNs. Cancer Immunol Immunother. 61, 1343-7.

Gillies S D, Lan Y, Brunkhorst B, Wong W K, Li Y, Lo K M. (2002). Bi-functional cytokine fusion proteins for gene therapy and antibody-targeted treatment of cancer. Cancer Immunol Immunother 51, 449-460

Halaas J L, Gajiwala K S, Maffei M, Cohen S L, Chait B T, Rabinowitz D, Lallone R L, Burley S K and Friedman J M. (1995). Weight-reducing effects of the plasma protein encoded by the obese gene. Science, 269, 543-6.

Hehlgans, T and Pfeffer, K (2005). The intriguing biology of the tumour necrosis factor/tumour necrosis factor receptor superfamily: players, rules and the games. Immunology. 115, 1-20.

Hieshima K, Imai T, Opdenakker G, Van Damme J, Kusuda J, Tei H, Sakaki Y, Takatsuki K, Miura R, Yoshie O and Nomiyama H. (1997). Molecular cloning of a novel human CC chemokine liver and activation-regulated chemokine (LARC) expressed in liver. Chemotactic activity for lymphocytes and gene localization on chromosome 2. J Biol Chem. 272, 5846-53.

Higgins S C, Jarnicki A G, Lavelle E C and Mills K H. (2006). TLR4 mediates vaccine-induced protective cellular immunity to *Bordetella pertussis*: role of IL-17-producing T cells. J Immunol. 177, 7980-9.

Idriss H T & Naismith J H (2000). TNF alpha and the TNF receptor superfamily: structure-function relationship(s). Microscopy research and technique 50, 184-95.

likuni N, Lam Q L, Lu L, Matarese G, La Cava A. (2008). Leptin and Inflammation. Curr Immunol Rev. 4, 70-79.

Jahn T, Zuther M, Friedrichs B, Heuser C, Guhlke S, Abken H, Hombach A A (2012). An IL12-IL2-antibody fusion protein targeting Hodgkin's lymphoma cells potentiates activation of NK and T cells for an anti-tumor attack. PLoS One 7:e44482.

Khader S A, Bell G K, Pearl J E, Fountain J J, Rangel-Moreno J, Cilley G E, Shen F, Eaton S M, Gaffen S L, Swain S L, Locksley R M, Haynes L, Randall T D and Cooper A M. (2007). IL-23 and IL-17 in the establishment of protective pulmonary CD4+ T cell responses after vaccination and during *Mycobacterium tuberculosis* challenge. Nat Immunol. 8, 369-77.

Krippner-Heidenreich A, Grunwald I, Zimmermann G, Kühnle M, Gerspach J, Sterns T, Shnyder S D, Gill J H, Männel DN, Pfizenmaier K and Scheurich P. (2008). Single-chain TNF, a TNF derivative with enhanced stability and antitumoral activity. J Immunol. 180, 8176-83.

Lu J, Peng Y, Zheng Z J, Pan J H, Zhang Y, Bai Y (2008). EGF-IL-18 fusion protein as a potential anti-tumor reagent by induction of immune response and apoptosis in cancer cells. Cancer Lett 260, 187-197.

Murzin A G, Lesk A M & Chothia C (1992). β-Trefoil fold: Patterns of structure and sequence in the Kunitz inhibitors interleukins-1β and 1α and fibroblast growth factors. Journal of Molecular Biology 223, 531-543.

Nicola N A & Hilton D J (1998). General classes and functions of four-helix bundle cytokines. Advances in protein chemistry 52, 1-65.

Nomiyama H, Osada N and Yoshie O. (2013). Systematic classification of vertebrate chemokines based on conserved synteny and evolutionary history. Genes Cells. 18,1-16.

O'Shaughnessy J A, Tolcher A, Riseberg D, Venzon D, Zujewski J, Noone M, Gossard M, Danforth D, Jacobson J, Chang V, Goldspiel B, Keegan P, Giusti R and Cowan K H. (1996). Prospective, randomized trial of 5-fluorouracil, leucovorin, doxorubicin, and cyclophosphamide chemotherapy in combination with the interleukin-3/granulocyte-macrophage colony-stimulating factor (GM-CSF) fusion protein (PIXY321) versus GM-CSF in patients with advanced breast cancer. Blood 87, 2205-2211

Penafuerte C, Bautista-Lopez N, Boulassel M R, Routy J P and Galipeau J (2009). The human ortholog of granulocyte macrophage colony-stimulating factor and interleukin-2 fusion protein induces potent ex vivo natural killer cell activation and maturation. Cancer Res 69, 9020-9028

Rafei M, Wu J H, Annabi B, Lejeune L, Francois M and Galipeau J (2007). A GMCSF and IL-15 fusokine leads to paradoxical immunosuppression in vivo via asymmetrical JAK/STAT signaling through the IL-15 receptor complex. Blood 109, 2234-2242

Rafei M, Hsieh J, Zehntner S, Li M, Forner K, Birman E, Boivin M N, Young Y K, Perreault C and Galipeau J. (2009a). A granulocyte-macrophage colony-stimulating factor and interleukin-15 fusokine induces a regulatory B cell population with immune suppressive properties. Nat Med 15, 1038-1045

Rafei M, Campeau P M, Wu J H, Birman E, Forner K, Boivin M N and Galipeau J. (2009b) Selective inhibition of CCR2 expressing lymphomyeloid cells in experimental autoimmune encephalomyelitis by a GM-CSF-MCP1 fusokine. J Immunol. 182, 2620-7.

Rafei M, Berchiche Y A, Birman E, Boivin M N, Young Y K, Wu J H, Heveker N, and Galipeau J. (2009c) An engineered GM-CSF-CCL2 fusokine is a potent inhibitor of CCR2-driven inflammation as demonstrated in a murine model of inflammatory arthritis. J Immunol. 183, 1759-66.

Rafei M, Deng J, Boivin M N, Williams P, Matulis S M, Yuan S, Birman E, Forner K, Yuan L, Castellino C, Boise L H, MacDonald T J and Galipeau J. (2011) A MCP1 fusokine with CCR2-specific tumoricidal activity. Mol Cancer. 10:121. doi: 10.1186/1476-4598-10-121.

Shaw M H, Kamada N, Kim Y G and Núñez G. (2012) Microbiota-induced IL-1β, but not IL-6, is critical for the development of steady-state TH17 cells in the intestine. J Exp Med. 209, 251-8.

Singh S P, Zhang H H, Foley J F, Hedrick M N and Farber J M. (2008) Human T cells that are able to produce IL-17 express the chemokine receptor CCR6. J Immunol. 180, 214-21.

Scatchard G. (1949). Ann New York Acad Sci 51, 660-72.

Stagg J, Wu J H, Bouganim N and Galipeau J. (2004). Granulocyte-macrophage colony-stimulating factor and interleukin-2 fusion cDNA for cancer gene immunotherapy. Cancer Res 64, 8795-8799
Sun P D & Davies D R. (1995). The cystine-knot growth-factor superfamily. Annual review of biophysics and biomolecular structure 24, 269-91.
Sutton C, Brereton C, Keogh B, Mills K H and Lavelle E C. (2006). A crucial role for interleukin (IL)-1 in the induction of IL-17-producing T cells that mediate autoimmune encephalomyelitis. J Exp Med. 203, 1685-91.
Weber H, Valenzuela D, Lujber G, Gubler M and Weissmann C. (1987). Single amino acid changes that render human IFN-alpha 2 biologically active on mouse cells. EMBO J. 6, 591-8.
Williams P, Bouchentouf M, Rafei M, Romieu-Mourez R, Hsieh J, Boivin M N, Yuan S, Forner K A, Birman E and Galipeau J. (2010a). A dendritic cell population generated by a fusion of GM-CSF and IL-21 induces tumor-antigen-specific immunity. J Immunol. 185, 7358-66.
Williams P, Rafei M, Bouchentouf M, Raven J, Yuan S, Cuerquis J, Forner K A, Birman E and Galipeau J. (2010b). A fusion of GMCSF and IL-21 initiates hyper-signaling through the IL-21Ralpha chain with immune activating and tumoricidal effects in vivo. Mol Ther 18, 1293-1301.
Ye P, Rodriguez F H, Kanaly S, Stocking K L, Schurr J, Schwarzenberger P, Oliver P, Huang W, Zhang P, Zhang J, Shellito J E, Bagby G J, Nelson S, Charrier K, Peschon J J and Kolls J K. (2001). Requirement of interleukin 17 receptor signaling for lung CXC chemokine and granulocyte colony-stimulating factor expression, neutrophil recruitment, and host defense. J Exp Med. 194, 519-27.

The invention claimed is:

1. A composition comprising a fusion protein comprising at least two cytokines, wherein the cytokines are single chain tumor necrosis factor alpha (scTNFα) and mutant leptin and wherein leptin comprises a mutation selected from L86S and L86N that reduces binding activity of leptin to its receptor as compared to wild type leptin and scTNFα is wild-type and provides cell-specific targeting that restores activity of the mutant leptin on the targeted cells.

2. The composition of claim 1, wherein the fusion protein further comprises a GGS linker.

* * * * *